(12) United States Patent
Ahn et al.

(10) Patent No.: US 11,006,520 B2
(45) Date of Patent: May 11, 2021

(54) STRETCHABLE ELECTRONICS AND METHOD FOR FABRICATING THE SAME

(71) Applicant: ELECTRONICS AND TELECOMMUNICATIONS RESEARCH INSTITUTE, Daejeon (KR)

(72) Inventors: Seongdeok Ahn, Daejeon (KR); Seung Youl Kang, Daejeon (KR); Seong Hyun Kim, Daejeon (KR); Hye Jin Kim, Daejeon (KR); Kang-Ho Park, Daejeon (KR); Jeong Ik Lee, Daejeon (KR); Young-deuk Jeon, Sejong-si (KR); Chi-Sun Hwang, Daejeon (KR); Jae Bon Koo, Daejeon (KR); Su Jae Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 278 days.

(21) Appl. No.: 16/217,629

(22) Filed: Dec. 12, 2018

(65) Prior Publication Data

US 2019/0342993 A1 Nov. 7, 2019

(30) Foreign Application Priority Data

May 3, 2018 (KR) ........................ 10-2018-0051480

(51) Int. Cl.
*H05K 1/00* (2006.01)
*H05K 1/02* (2006.01)
*H05K 1/18* (2006.01)
*H05K 3/30* (2006.01)
(Continued)

(52) U.S. Cl.
CPC .......... *H05K 1/0283* (2013.01); *H05K 1/181* (2013.01); *H05K 3/30* (2013.01); *H01L 41/0533* (2013.01); *H01L 41/09* (2013.01); *H05K 2201/09045* (2013.01); *H05K 2201/10083* (2013.01); *H05K 2201/10151* (2013.01); *H05K 2201/10545* (2013.01)

(58) Field of Classification Search
CPC ........ H05K 1/0283; H05K 1/181; H05K 3/30; H05K 2201/09045; H05K 2201/10083; H05K 2201/10151; H05K 2201/10545; H01L 41/0533; H01L 41/09
See application file for complete search history.

(56) References Cited

U.S. PATENT DOCUMENTS

| | | | |
|---|---|---|---|
| 9,177,821 | B2 | 11/2015 | Jung et al. |
| 9,869,807 | B2 | 1/2018 | Kim et al. |
| 10,603,690 | B2 | 3/2020 | Zadesky et al. |

(Continued)

FOREIGN PATENT DOCUMENTS

| | | |
|---|---|---|
| CN | 205104519 U | 3/2016 |
| CN | 105606291 A | 5/2016 |
| CN | 107710885 A | 2/2018 |

*Primary Examiner* — Pete T Lee
(74) *Attorney, Agent, or Firm* — Rabin & Berdo, P.C.

(57) ABSTRACT

Provided is stretchable electronics. The stretchable electronics includes stretchable substrate, first support patterns disposed on a first surface of the stretchable substrate, and output devices disposed on the first patterns, respectively. The first support patterns are arranged in a first direction and a second direction, which are parallel to an extension direction of the substrate, and each of the output devices generates an output stimulation.

19 Claims, 19 Drawing Sheets

(51) Int. Cl.
 *H01L 41/053* (2006.01)
 *H01L 41/09* (2006.01)

(56) References Cited

U.S. PATENT DOCUMENTS

| | | | |
|---|---|---|---|
| 2013/0041235 | A1 | 2/2013 | Rogers et al. |
| 2014/0340857 | A1* | 11/2014 | Hsu ..................... A61B 5/6846 361/749 |
| 2015/0147854 | A1 | 5/2015 | Jung et al. |
| 2016/0023245 | A1 | 1/2016 | Zadesky et al. |
| 2017/0005077 | A1* | 1/2017 | Kim ..................... G06F 1/1643 |
| 2017/0049913 | A1 | 2/2017 | Yu et al. |
| 2017/0114314 | A1 | 4/2017 | Kim et al. |
| 2017/0145371 | A1 | 5/2017 | Song et al. |
| 2018/0376585 | A1* | 12/2018 | Aleksov .............. H01L 23/5387 |

\* cited by examiner

STRETCHABLE ELECTRONICS AND METHOD FOR FABRICATING THE SAME

CROSS-REFERENCE TO RELATED APPLICATIONS

This U.S. non-provisional patent application claims priority under 35 U.S.C. § 119 of Korean Patent Application No. 10-2018-0051480, filed on May 3, 2018, the entire contents of which are hereby incorporated by reference.

BACKGROUND

The present disclosure relates to stretchable electronics and a method for fabricating the same.

The tactile sense refers to the various senses felt through human skin. The various types of tactile receptors present under the skin treat various sensations such as a pressure, texture, a temperature, and pain, which are felt on the skin. Electro-skin technologies that make feeling of various senses may be expected to be applicable to various industrial fields such as AR/VR fields that provide various senses in virtual environment similar to real world, bio-diagnosis/treatment requiring human tactile ability, healthcare system such as health and medical care such as surgical soft robot, disaster/structure, defense industry, and the like. Thus, stretchable electronic skin, which is similar to human skin, senses tactile information, and outputs the sensed information to the skin, is needed.

To treat various senses such as a pressure, texture, a temperature, and pain felt on the skin, a tactile sensor technology similar to the human skin sensory receptor and an actuator technology capable of transmitting and outputting various senses to human through the skin have to be fused into stretchable electronic skin.

Also, the human skin has an array of sensory receptors, which senses the physical quantities of various senses, and the electronic skin has also to be mounted in the elastic skin of the electronic circuit to be acquired and treated from the tactile sensors that perform such a function.

Thus, there is a demand for the development of an elastic skin element having a sensor that senses a variety of tactility similarly to the actual skin structure of a person, and an actuator capable of transmitting and outputting the sensed tactility to the human skin.

SUMMARY

The present disclosure provides stretchable electronics that senses tactility and transmits stimulation.

The present disclosure provides a method for fabricating stretchable electronics that senses tactility and transmits stimulation.

However, objects of the inventive concept are not limited to the abovementioned objects.

An embodiment of the inventive concept provides stretchable electronics includes: a stretchable substrate; first support patterns disposed on a first surface of the stretchable substrate; and output devices disposed on the first support patterns, respectively, wherein the first support patterns are arranged in a first direction and a second direction, which are parallel to an extension direction of the substrate, and each of the output devices generates an output stimulation.

In an embodiment, the first support patterns may protrude from the first surface of the stretchable substrate.

In an embodiment, each of the first support patterns may have a thickness greater than that of the stretchable substrate.

In an embodiment, each of the first support patterns may be made of a rigid material and include the same material as that within the stretchable substrate.

In an embodiment, the first surface may include a wavy surface.

In an embodiment, the stretchable electronics may further include lines disposed on the stretchable substrate and the first support patterns, wherein the lines may extend along the wavy surface of the first surface.

In an embodiment, each of the lines may have a straight line shape on a side surface of the first support patterns and have a winding shape on the first surface.

In an embodiment, the lines may include: first lines extending in the first direction; and second lines extending in the second direction, wherein the output devices may be disposed on areas on which the first lines and the second lines cross each other, respectively.

In an embodiment, at least one of the output devices may include: actuators disposed on the first support patterns; and a diaphragm disposed on the actuators, wherein the diaphragm may be spaced apart from the first support patterns by the actuators, and the diaphragm may vibrate by movement of the actuators.

In an embodiment, the stretchable electronics may further include input devices disposed on the first surface, wherein the input devices and the output devices may be alternately arranged in the first direction and the second direction, and the input devices may sense an input stimulation.

In an embodiment, the stretchable electronics may further include second support patterns disposed between the input devices and the first surface, wherein the second support patterns may protrude from the first surface.

In an embodiment, the stretchable electronics may further include: an output signal control unit; and an input signal control unit, wherein the output devices may generate the output stimulation on the basis of an output signal provided from the output signal control unit, and the input devices may generate input signals corresponding to the input stimulation to provide the input signals to the input signal control unit, wherein the output signal may include position information and intensity information of the output stimulation, and the input signal may include position information and intensity information of the input stimulation.

In an embodiment, the stretchable electronics may further include input devices disposed on a second surface of the stretchable substrate, which faces the first surface, wherein the input devices may be alternately arranged in the first direction and the second direction, and the input devices may sense an input stimulation.

In an embodiment, the stretchable electronics may further include second support patterns disposed between the input devices and the second surface, wherein the second support patterns may protrude from the second surface.

In an embodiment, each of the second support patterns may be made of a rigid material and include the same material as that within the stretchable substrate.

In an embodiment, the second surface may include a wavy surface.

In an embodiment of the inventive concept, a method for fabricating stretchable electronics includes: forming an output device structure on a first carrier substrate; separating the output device structure from the first carrier substrate so as to be transferred to a first surface of the substrate; forming an input device structure on a second carrier substrate; and separating the input device structure from the second carrier substrate so as be transferred to a second surface of the substrate, which faces the first surface, wherein the output device structure comprises output devices generating an output stimulation, and the input device structure comprises input devices receiving an input stimulation.

In an embodiment, the method may further include providing tensile force to the substrate while the output device structure and the input device structure are transferred to the substrate, wherein the substrate may include a pre-stretched substrate.

In an embodiment, the method may further include removing the tensile force from the substrate to form a wavy structure on the substrate after the transferring of the output device structure and the input device structure on the substrate.

In an embodiment, the substrate may include an elastomer.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
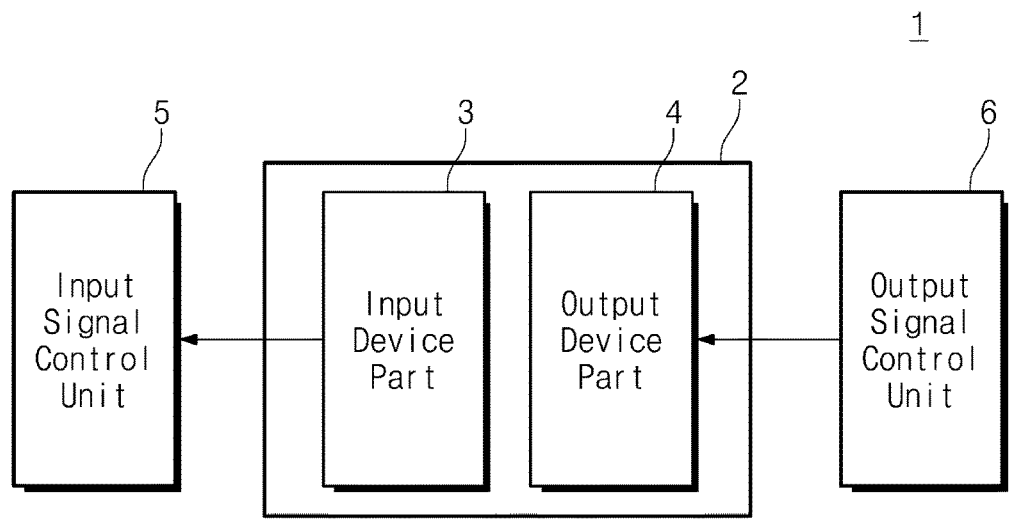
FIG. 1 is a block diagram of stretchable electronics according to exemplary embodiments of the inventive concept.

Exemplary embodiments of technical ideas of the inventive concept will be described with reference to the accompanying drawings so as to sufficiently understand constitutions and effects of the inventive concept. The technical ideas of the inventive concept may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims.

Like reference numerals refer to like elements throughout. The embodiments in the detailed description will be described with perspective views, front views, cross-sectional views, and/or conceptual views as ideal exemplary views of the inventive concept. In the figures, the dimensions of regions are exaggerated for effective description of the technical contents. Areas exemplified in the drawings have general properties and are used to illustrate a specific shape of a device. Thus, this should not be construed as limited to the scope of the inventive concept. Also, although various terms are used to describe various components in various embodiments of the inventive concept, the component are not limited to these terms. These terms are only used to distinguish one component from another component. Embodiments described and exemplified herein include complementary embodiments thereof.

In the following description, the technical terms are used only for explaining a specific exemplary embodiment while not limiting the inventive concept. In this specification, the terms of a singular form may comprise plural forms unless specifically mentioned. The meaning of 'comprises' and/or 'comprising' does not exclude other components besides a mentioned component.

Hereinafter, the present disclosure will be described in detail by explaining preferred embodiments of the technical ideas of the inventive concept with reference to the attached drawings.

FIG. 1 is a block diagram of stretchable electronics according to exemplary embodiments of the inventive concept.

Referring to FIG. 1, stretchable electronics including a device unit 2, an input signal control unit 5, and an output signal control unit 6 may be provided. The device unit 2 may include an input device part 3 and an output device part 4. The input device part 3 may sense an input stimulation. For example, the input stimulation may be one of a tactile stimulation, a warm stimulation, a cold stimulation, a nociceptive stimulation, and a tensile stimulation. The input device part 3 may generate an input signal corresponding to the input stimulation. For example, the input stimulation may be one of a tactile sensation signal, a warm sensation signal, a cold sensation signal, a nociceptive sensation signal, and a tensile sensation signal. The input device part 3 may provide an input side to the input signal control unit 5.

The input signal control unit 5 may generate input data on the basis of the input signal. The input data may include a generated position of the input stimulation and intensity information of the input stimulation. In the exemplary embodiments, the input signal control unit 5 may transmit the input data to the outside of the stretchable electronics 1.

The output device unit 4 may receive an output signal from the output signal control unit 6. The output device unit 4 may generate an output stimulation on the basis of the output signal. For example, the output stimulation may be one of a tactile stimulation, a warm stimulation, a cold stimulation, a nociceptive stimulation, and a tensile stimulation. The output signal may correspond to the output stimulation. For example, the output signal may be one of a tactile sensation signal, a warm sensation signal, a cold sensation signal, a nociceptive sensation signal, and a tensile sensation signal.

The output signal control unit 6 may generate an output signal on the basis of output data. The output data may include a generated position of the output stimulation and intensity information of the output stimulation. In the exemplary embodiments, the output signal control unit 6 may receive the output data from the outside of the output signal control unit 6.

Figure 2:
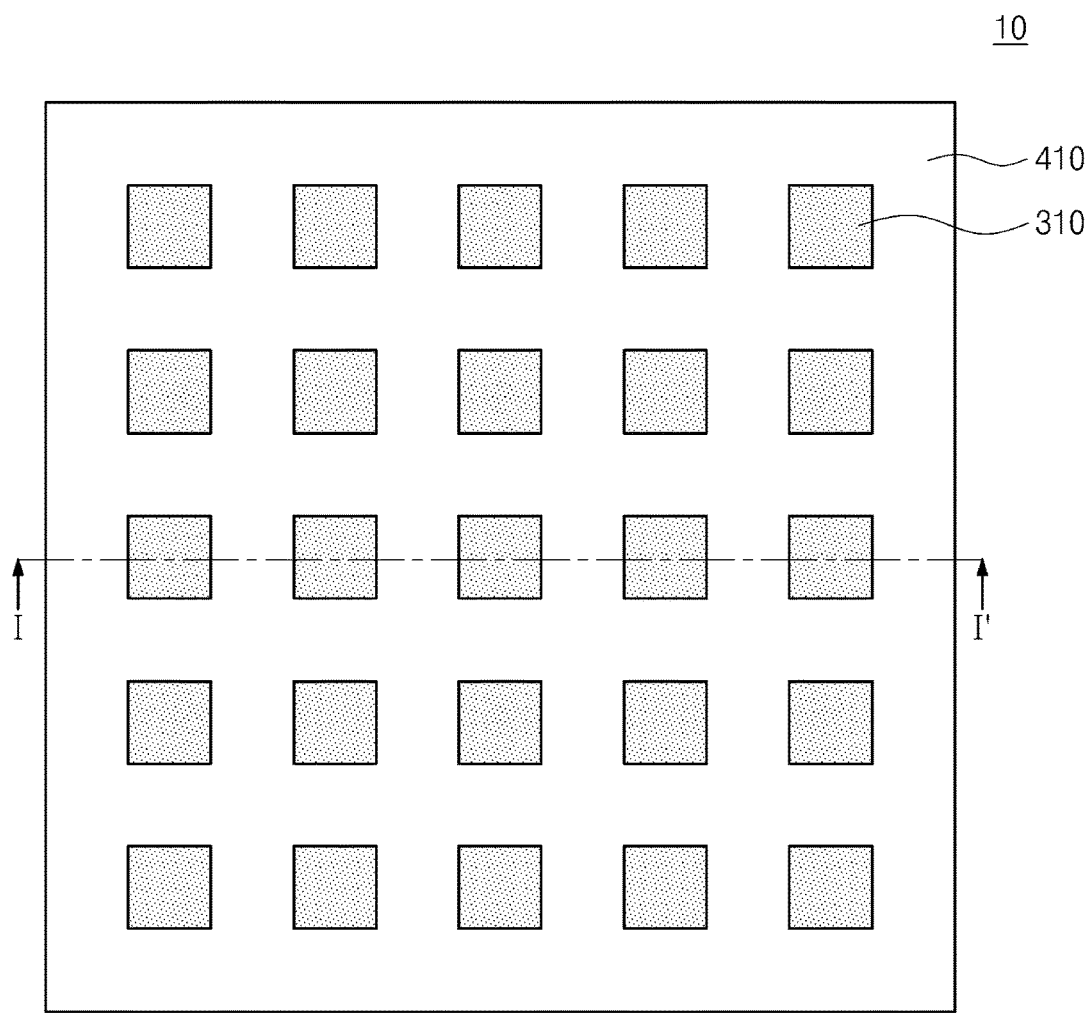
FIGS. 2 and 3 are plan and bottom views of the stretchable electronics according to exemplary embodiments of the inventive concept.
Figure 3:
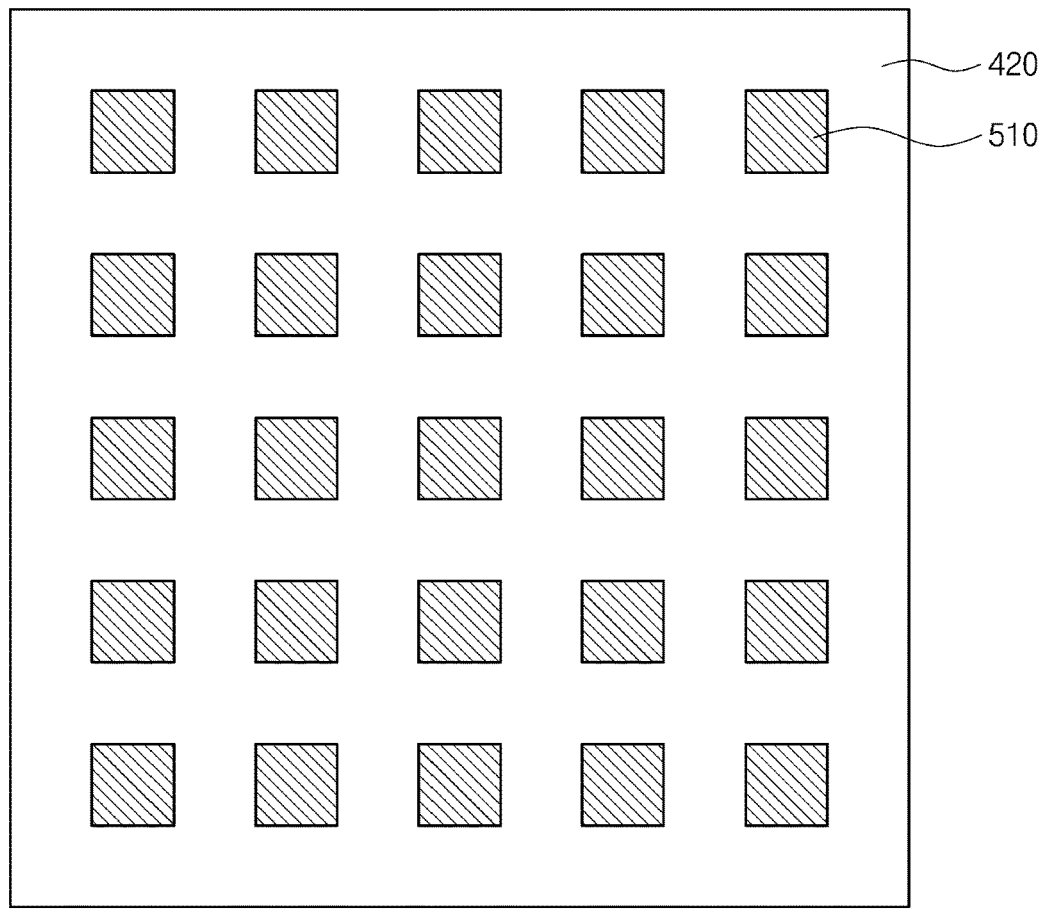
Figure 4:
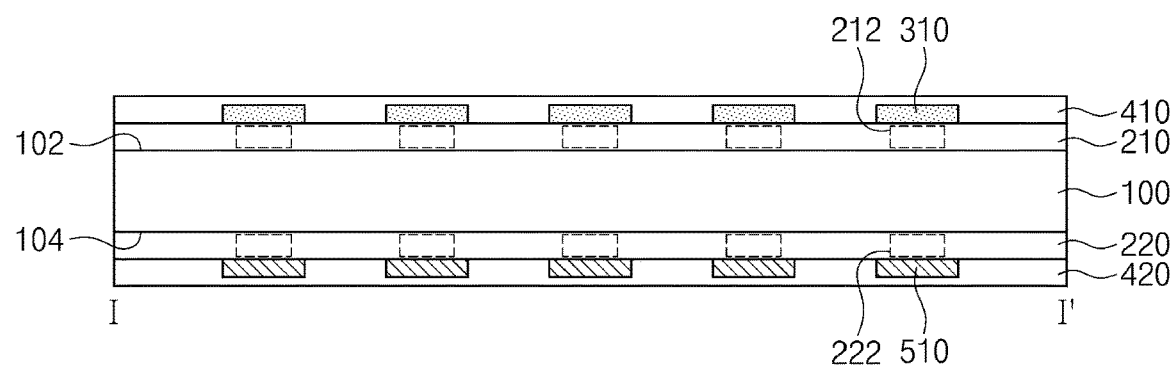
FIG. 4 is a cross-sectional view taken along line I-I' of FIG. 2.

FIGS. 2 and 3 are plan and bottom views of the stretchable electronics according to exemplary embodiments of the inventive concept. FIG. 4 is a cross-sectional view taken along line I-I' of FIGS. 2 and 3.

Referring to FIGS. 2 to 4, stretchable electronics 10 including a substrate 100, an output control layer 210, output devices 310, a first protection layer 410, an input control layer 220, input devices 510, and a second protection layer 420 may be provided.

The substrate 100 may be a stretchable substrate. For example, the substrate 100 may be stretchable from its initial shape by tensile force. When the tensile force is removed, the substrate 100 may be returned to its initial shape. The substrate 100 may have a sufficient thickness to have stretchability. For example, the substrate 100 may have a thickness of about 1 μm to about 2 μm. For example, the substrate 100 may include PI, PDMS, Ecoflex, or a combination thereof. The substrate 100 may have a first surface 102 and a second surface 104, which face each other.

The output control layer 210 may be disposed on the first surface 102. The output control layer 210 may have stretchability. The output control layer 210 may include output control devices 212 and lines (not shown) electrically connecting the output control devices 212 to each other. The output control devices 212 may be arranged in a direction parallel to the first surface 102. The output control devices 212 may be electrically connected to the output devices 310 to control the output devices 310. For example, the output control devices 212 may receive an output signal from the output signal control unit (see reference numeral 6 of FIG. 1) described with reference to FIG. 1 to control the output devices 310 on the basis of the output signal.

The output devices 310 may be disposed on the output control layer 210. Each of the output devices 310 may extend in parallel to a first incident surface 102. The output devices 310 may be controlled by the output control devices 212 to generate the output stimulation. For example, the output devices 310 may generate the tactile stimulation, the warm stimulation, the cold stimulations, the nociceptive stimulation, or the tensile stimulation. The output stimulation generated from the output devices 310 may be transmitted to a user using the stretchable electronics 10.

The first protection layer 410 may be disposed on the output control layer 210 to cover the output devices 310. The first protection layer 410 may protect the output control layer 210 and the output devices 310. For example, the first protection layer 410 may include an insulation material having the stretchability.

The input control layer 220 may be disposed on the second surface 104. The input control layer 220 may have the stretchability. The input control layer 220 may include input control devices 222 and lines (not shown) electrically connecting the input control devices 222 to each other. The input control devices 222 may be arranged in a direction parallel to the second surface 104. When the input devices 510 sense the input stimulation, the input control devices 222 may generate an input signal corresponding to the input stimulation. The input control devices 222 may be provided in the input signal control unit (see reference numeral 5 of FIG. 1) described with reference to FIG. 1.

The input devices 510 may be disposed on the input control layer 220. The input devices 510 may be arranged in a direction parallel to the second surface 104. The input devices 510 may sense an external input stimulation of the input devices 510. For example, the input devices 510 may the tactile stimulation, the warm stimulation, the cold stimulations, the nociceptive stimulation, or the tensile stimulation. When the input devices 510 sense a pressure stimulation, each of the input devices 510 may include a pressure sensitive rubber (PSR) or a piezo-electric layer (PEL). When the input devices 510 sense the tensile stimulation, each of the input devices 510 may include a poezoresistive strain sensor. The input devices 510 may be electrically connected to the input control devices 222. Thus, when the input devices 510 sense the input stimulation, the input control devices 222 may generate the input signal.

The second protection layer 420 may be disposed on the input control layer 220 to cover the input devices 510. The second protection layer 420 may protect the input control layer 220 and the input devices 510. For example, the second protection layer 420 may include an insulation material having the stretchability.

The stimulation may be outputted and inputted by the output devices 310 and the input device 510 according to the inventive concept. Each of the substrate 100, the output control layer 210, the input control layer 220, the first protection layer 410, and the second protection layer 420 may have the stretchability. Thus, when the tensile force is provided to the stretchable electronics 10, the stretchable electronics 10 may be deformed. As a result, the stretchable electronics 10 into/from which the stimulation is inputted/outputted may be provided.

Figure 5:
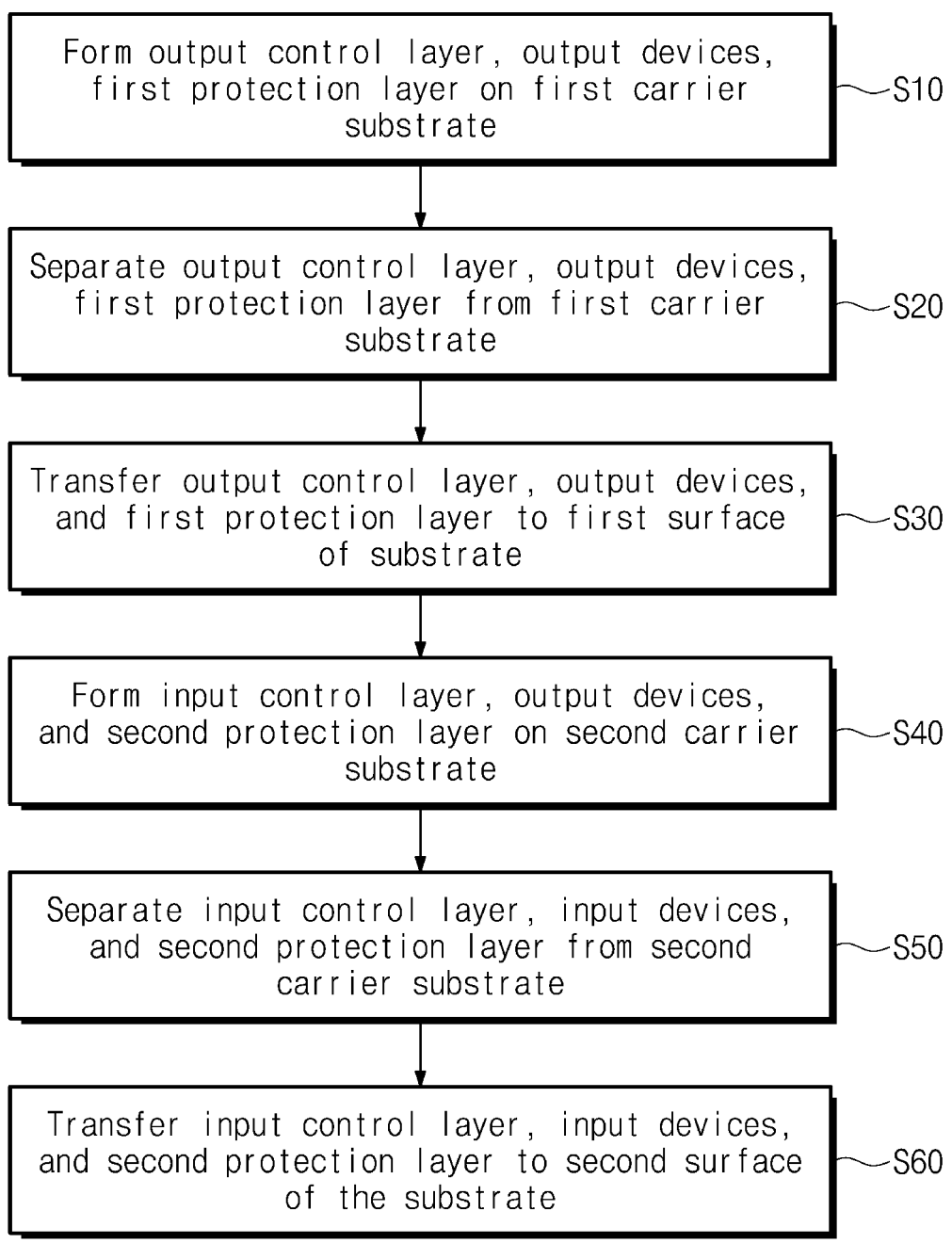
FIG. 5 is a flowchart for explaining a method for fabricating the stretchable electronics according to exemplary embodiments of the inventive concept.
Figure 6:
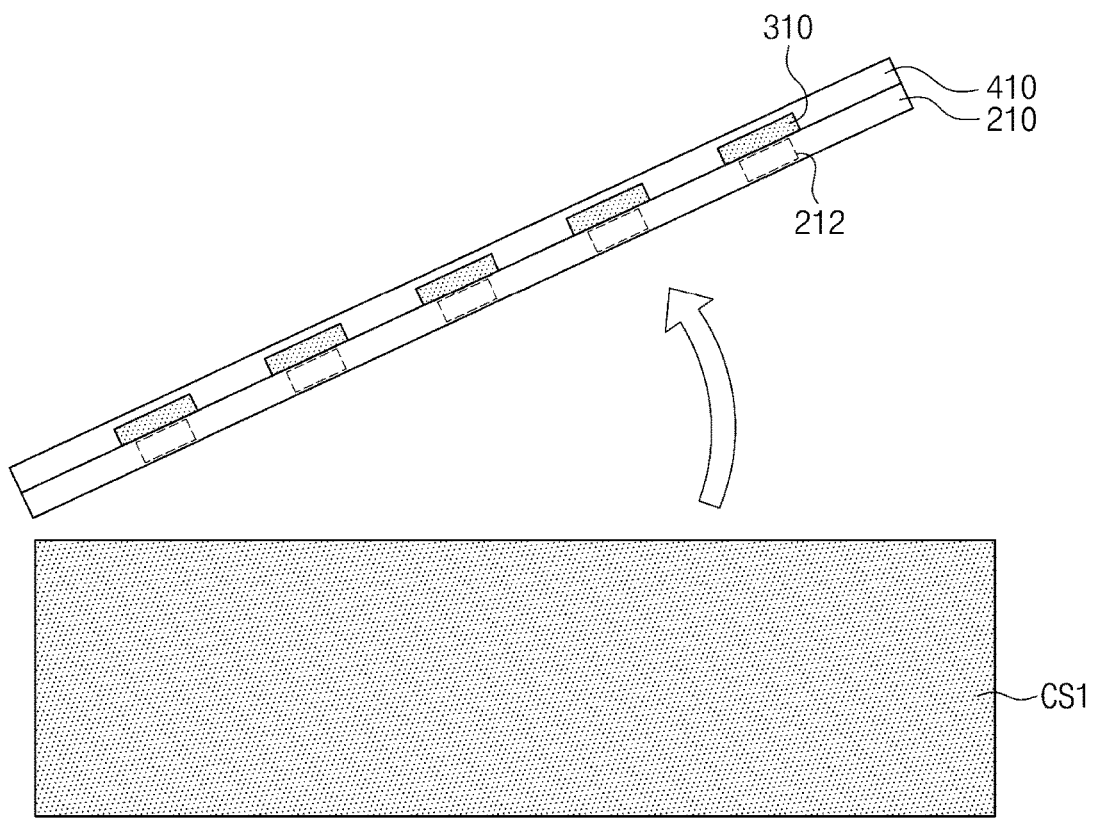
FIGS. 6 to 8 are cross-sectional views for explaining the method for fabricating the stretchable electronics according to exemplary embodiments of the inventive concept.
Figure 7:
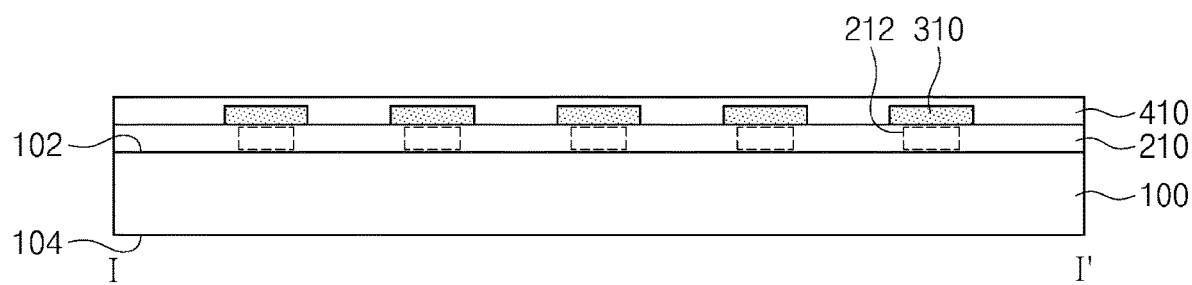
Figure 8:
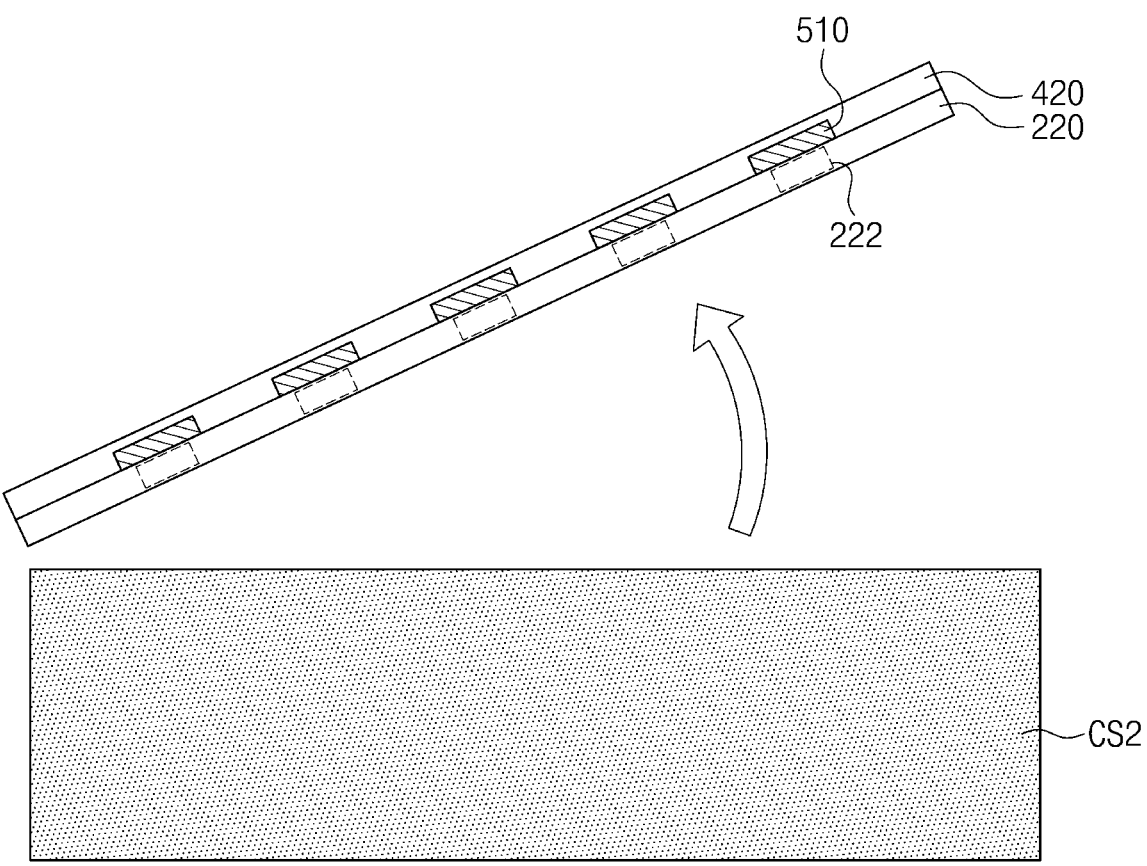

FIG. 5 is a flowchart for explaining a method for fabricating the stretchable electronics according to exemplary embodiments of the inventive concept. FIGS. 6 to 8 are cross-sectional views taken along line I-I' of FIG. 2 so as to explain the method for fabricating the stretchable electronics according to exemplary embodiments of the inventive concept. For briefness of descriptions, substantially the same description as those described with reference to FIGS. 2 to 4 will be omitted.

Referring to FIGS. 5 and 6, an output control layer 210, output devices 310, and a first protection layer 410 may be formed on a first carrier substrate CS1 (S10). The output control layer 210 may include output control devices 212.

The output control devices 212 may be substantially the same as the output control device 212 described with reference to FIG. 3.

The output control layer 210, the output devices 310, and the first protection layer 410 may be detachable from the first carrier substrate CS1 (S20). For example, the detachment process may include a process of removing a sacrificial layer (not shown) disposed between the first carrier substrate CS1 and the output control layer 210.

Referring to FIGS. 5 and 7, the output control layer 210, the output devices 310, and the first protection layer 410 may be transferred to the first surface 102 of the substrate 100 (S30). For example, the transfer process may include a process of bonding the output control layer 210 to the substrate 100 by using an adhesion layer (not shown). The substrate 100 may have stretchability. The substrate 100 may be substantially the same as that 100 described with reference to FIGS. 2 to 4.

Referring to FIGS. 5 and 8, an input control layer 220, input devices 510, and a second protection layer 420 may be formed on a second carrier substrate CS2 (S40). The input control layer 220 may include input control devices 222. The input control devices 222 may be substantially the same as the input control device 222 described with reference to FIG. 3.

The input control layer 220, the input devices 510, and the second protection layer 420 may be detachable from the second carrier substrate CS2 (S50). For example, the detachment process may include a process of removing a sacrificial layer (not shown) disposed between the second carrier substrate CS2 and the input control layer 220.

Referring to FIGS. 4 and 5, the input control layer 220, the input devices 510, and the second protection layer 420 may be transferred to the second surface 104 of the substrate 100 (S60). For example, the transfer process may include a process of bonding the input control layer 220 to the substrate 100 by using an adhesion layer (not shown).

According to the inventive concept, the stretchable electronics 10 may be provided through the simple process.

Figure 9:
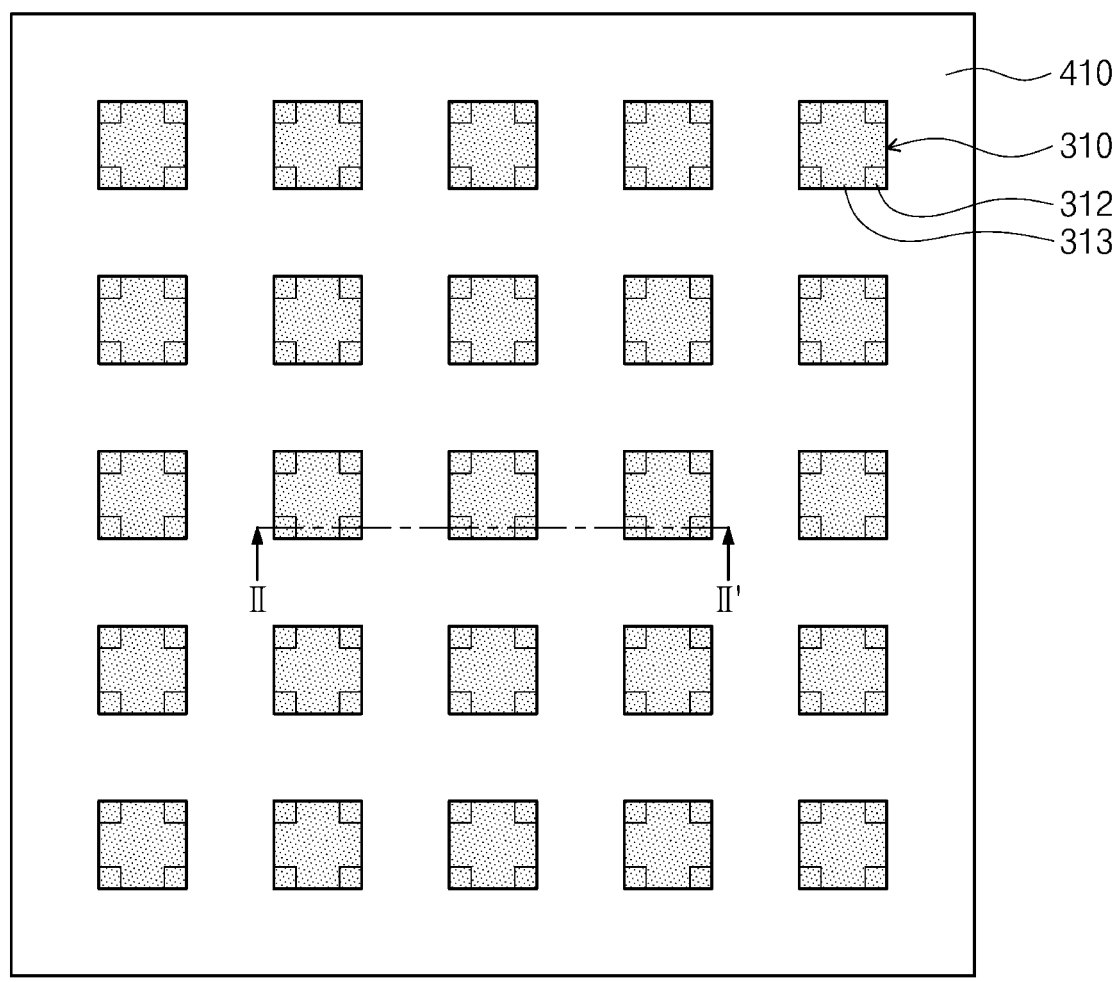
FIG. 9 is a plan view of stretchable electronics according to exemplary embodiments of the inventive concept.
Figure 10:
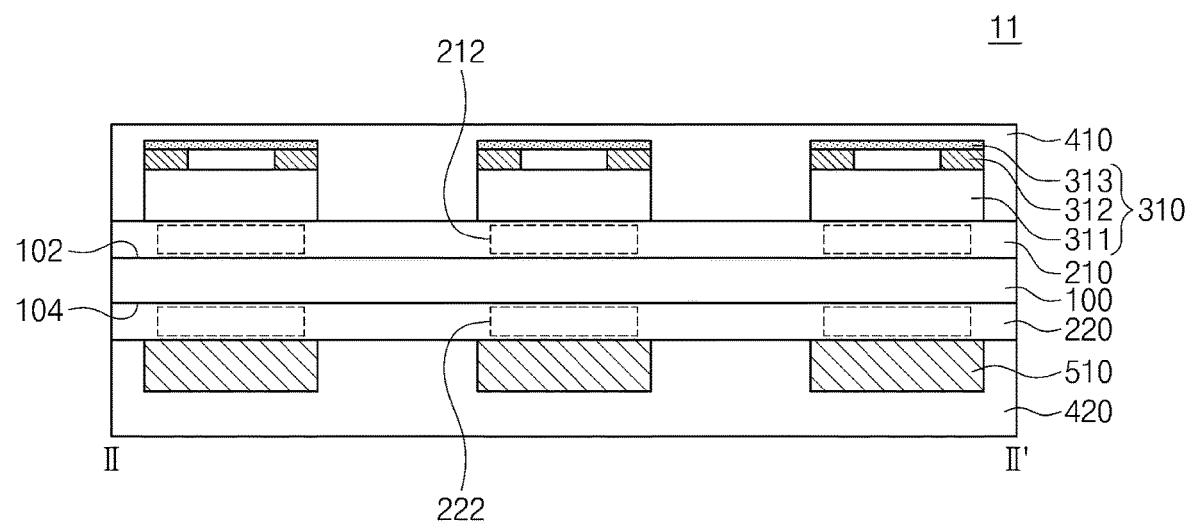
FIG. 10 is a cross-sectional view taken along line II-II' of FIG. 9.

FIG. 9 is a plan view of stretchable electronics according to exemplary embodiments of the inventive concept. FIG. 10 is a cross-sectional view taken along line II-II' of FIG. 9. For briefness of descriptions, substantially the same description as those described with reference to FIGS. 2 to 4 will be omitted.

Referring to FIGS. 9 to 10, stretchable electronics 11 including a substrate 100, an output control layer 210, output devices 310, a first protection layer 410, an input control layer 220, input devices 510, and a second protection layer 420 may be provided. The substrate 100, the output control layer 210, the first protection layer 410, the input control layer 220, the input devices 510, and the second protection layer 420 may be substantially the same as the substrate 100, the output control layer 210, the first protection layer 410, the input control layer 220, the input devices 510, and the second protection layer 420, which are described with reference to FIGS. 2 to 4.

Each of the output devices 310 may include an auxiliary substrate 311, actuators 312, and a diaphragm 313. The auxiliary substrate 311 may be disposed on the output control layer 210. The auxiliary substrate 311 may be bonded to a top surface of the output control layer 210. That is, a bottom surface of the auxiliary substrate 311 may directly contact the top surface of the output control layer 210. The auxiliary substrate 311 may have a rigid material. Thus, when the substrate 100 is deformed, the auxiliary substrate 311 may be maintained in shape without being deformed. The auxiliary substrate 311 may include substantially the same material as the substrate 100. For example, the auxiliary substrate 311 may include PI, PDMS, Ecoflex, or a combination thereof. The auxiliary substrate 311 may have a thickness greater than that of the substrate 100. Since the auxiliary substrate 311 has a rigid property, the auxiliary substrate 311 may have a sufficient thickness.

The actuators 312 may be disposed on the auxiliary substrate 311. The actuators 312 may be spaced apart from each other in a direction parallel to a top surface of the auxiliary substrate 311. For example, four actuators 312 disposed adjacent to vertexes of the auxiliary substrate 311 are illustrated in FIG. 9. Each of the actuators 312 may have a size and number, which are selected as desired. The actuators 312 may generate vibration. For example, each of the actuators 312 may include a piezoelectric element. The piezoelectric element may include an upper electrode, a lower electrode, and a piezoelectric thin film disposed between the upper electrode and the lower electrode. The upper electrode may be disposed adjacent to the diaphragm 313. The lower electrode may be disposed adjacent to the auxiliary substrate 311.

Different voltages may be applied to the upper electrode and the lower electrode to apply an electric field to the piezoelectric thin film. The piezoelectric thin film may be deformed by the electric field. The voltages applied to the upper electrode and the lower electrode may be adjusted to allow the piezoelectric thin film to vibrate. For example, the piexoelectric thin film may include at least one selected from PZT, PLZT, PMN-PT, PZN-PT, PYN-PT, PIN-PT, PVDF, PVDF-TrFE, PVDF-TFE, PVC, PAN, PPEN, polyamides, ZnO, AlN, $BaTiO_3$, $LiNbO_3$, and $LiTaO_3$. For example, each of the upper electrode and the lower electrode may include at least one selected from ITO, Mo, Al, Ag, Cu, Ti/Au, Ti/Pt, graphene, CNT, metal nanoparticles, PEDOT, and PEDOT-PSS.

The diaphragm 313 may be disposed on the actuators 312. The diaphragm 313 may extend in the direction parallel to the top surface of the auxiliary substrate 311. The diaphragm 313 may contact a top surface of each of the actuators 312. For example, the diaphragm 313 may contact the upper electrode of each of the actuators 312. The diaphragm 313 may overlap the actuators 312 in a direction that is perpendicular to the top surface of the auxiliary substrate 311. The diaphragm 313 may be spaced apart from the auxiliary substrate 311 by the actuators 312. Thus, an air gap may be provided between the diaphragm 313 and the auxiliary substrate 311. For example, the diaphragm 313 may include at least one selected from a metal thin film, polyimide, PMMA, PDMS, silicone, and Ecoflex.

In general, when the actuators are directly disposed on the stretchable substrate, the vibration of the actuator may be absorbed to the stretchable substrate. Thus, efficiency in which the vibration of the actuators is outputted to the outside of the stretchable electronics may be reduced.

The auxiliary substrate 311 according to the inventive concept may not absorb the vibration of the actuators 312. Thus, the vibration output efficiency of the stretchable electronics 11 may be improved.

Figure 11:
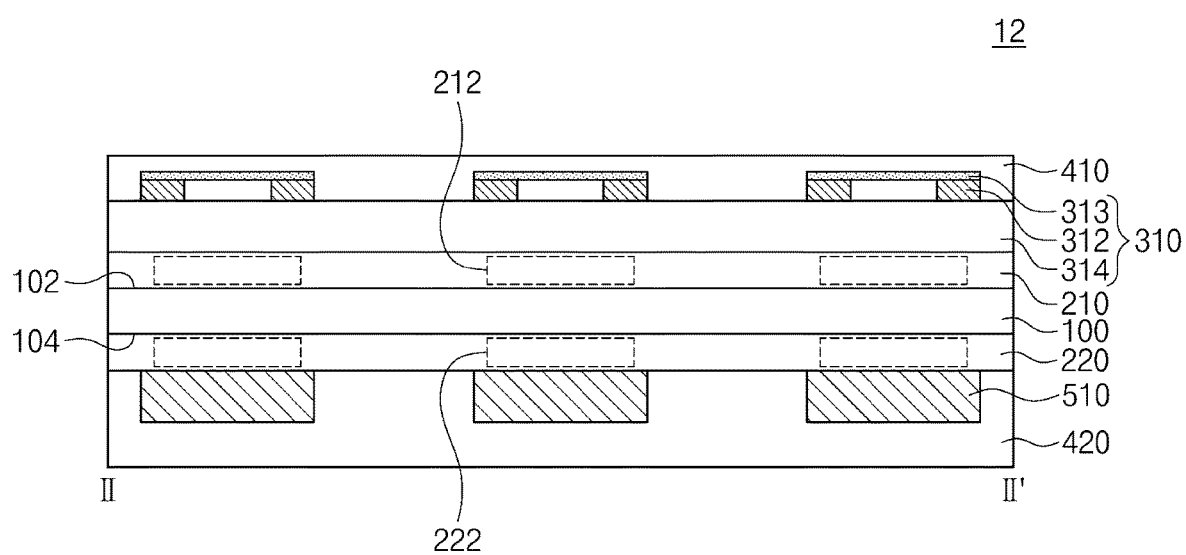
FIG. 11 is a cross-sectional view taken along line II-II' of FIG. 9 according to exemplary embodiments of the inventive concept.

FIG. 11 is a cross-sectional view taken along line II-II' of FIG. 9 in the stretchable electronics according to exemplary embodiments of the inventive concept. For briefness of descriptions, substantially the same description as those described with reference to FIGS. 9 and 10 will be omitted.

Referring to FIG. 11, stretchable electronics 12 including a substrate 100, an output control layer 210, output devices 310, a first protection layer 410, an input control layer 220, input devices 510, and a second protection layer 420 may be provided. The substrate 100, the output control layer 210, the first protection layer 410, the input control layer 220, and the second protection layer 420 may be substantially the same as the substrate 100, the output control layer 210, the first protection layer 410, the input control layer 220, and the second protection layer 420, which are described with reference to FIGS. 9 and 10.

Each of the output devices 310 may include an auxiliary film 314, an actuator 312, and a diaphragm 313. The actuator 312 and the diaphragm 313 may be substantially the same as the actuator 312 and the diaphragm 313, which are described with reference to FIGS. 9 and 10.

The auxiliary film 314 may be disposed on the output control layer 210. The auxiliary film 314 may be bonded to a top surface of the output control layer 210. That is, a bottom surface of the auxiliary film 314 may directly contact the top surface of the output control layer 210. The auxiliary film 314 may extend in the direction parallel to the top surface of the output control layer 210. The auxiliary film 314 may have a rigid material. The auxiliary substrate 311 may include substantially the same material as the substrate 100. For example, the auxiliary substrate 311 may include PI, PDMS, Ecoflex, or a combination thereof. The auxiliary substrate 311 may have a thickness greater than that of the substrate 100. Since the auxiliary substrate 311 has a rigid property, the auxiliary substrate 311 may have a sufficient thickness.

The auxiliary film 314 according to the inventive concept may not absorb the vibration of the actuators 312. Thus, the vibration output efficiency of the stretchable electronics 12 may be improved.

Figure 12:
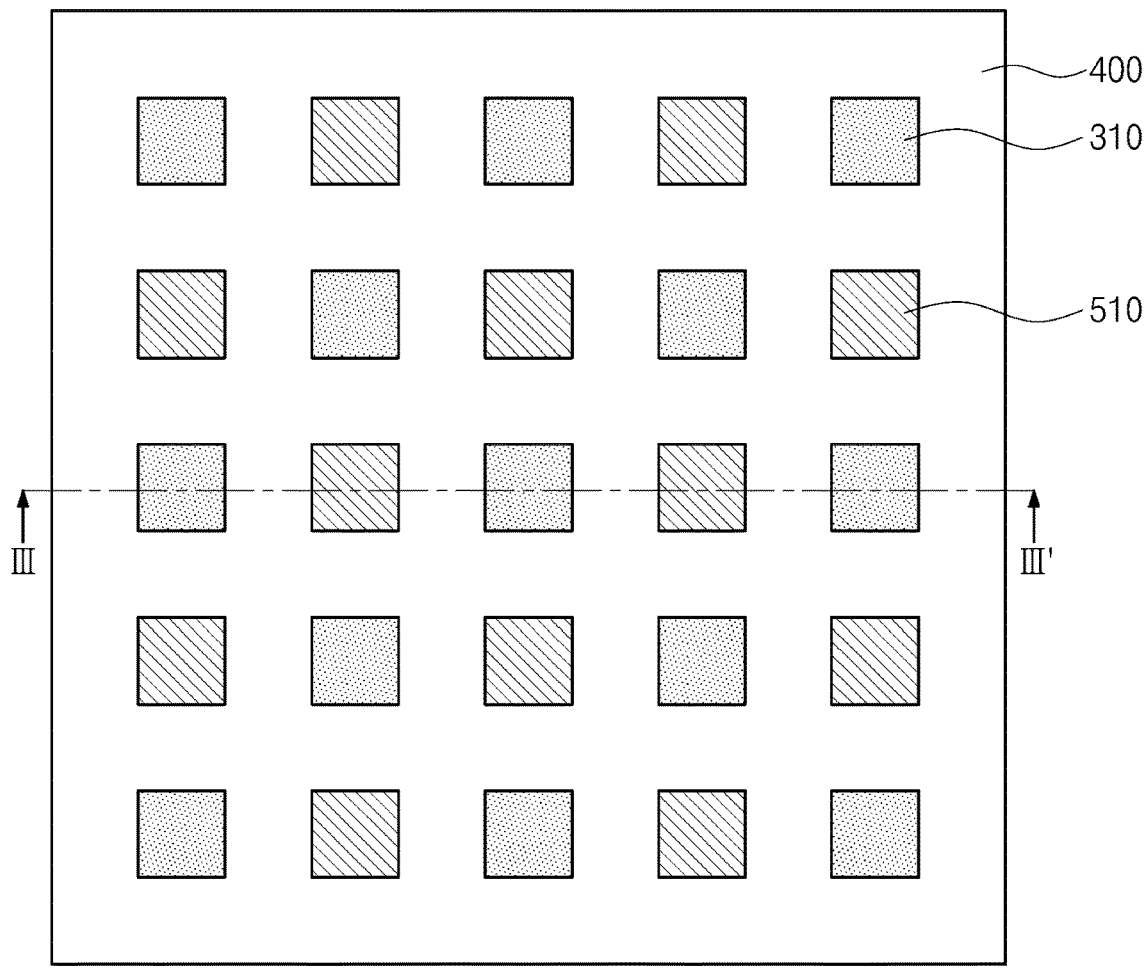
FIG. 12 is a plan view of stretchable electronics according to exemplary embodiments of the inventive concept.
Figure 13:
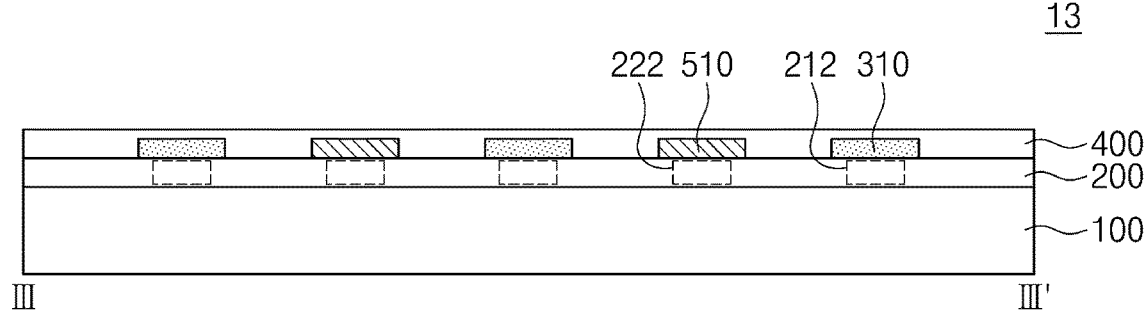
FIG. 13 is a cross-sectional view taken along line III-III' of FIG. 12.

FIG. 12 is a plan view of stretchable electronics according to exemplary embodiments of the inventive concept. FIG. 13 is a cross-sectional view taken along line III-III' of FIG. 12. For briefness of descriptions, substantially the same description as those described with reference to FIGS. 2 to 4 will be omitted.

Referring to FIGS. 12 and 13, stretchable electronics 13 including a substrate 100, a control layer 200, output devices 310, input devices 510, and a protection layer 400 may be provided. The substrate 100 may be substantially the same as that 100 described with reference to FIGS. 2 to 4. The control layer 200 may be disposed on the substrate 100. The control layer 200 may extend in a direction parallel to a top surface of the substrate 100. The control layer 200 may include output control devices 212 and input control devices 222.

The output control devices 212 and the input control devices 222 may be alternately arranged in the direction parallel to the top surface of the substrate 100. The output control devices 212 may control the output devices 310, respectively. The input control devices 222 may control the input devices 510, respectively.

The output devices 310 and the input devices 510 may be disposed on the control layer 200. The output devices 310 and the input devices 510 may be alternately arranged in the direction parallel to the top surface of the substrate 100. The output devices 310 and the input devices 510 may be substantially the same as the output devices 310 and the input devices 510, which are described with reference to FIGS. 2 to 4.

According to the inventive concept, the stretchable electronics 13 through which the stimulation is outputted and inputted may be provided.

Figure 14:
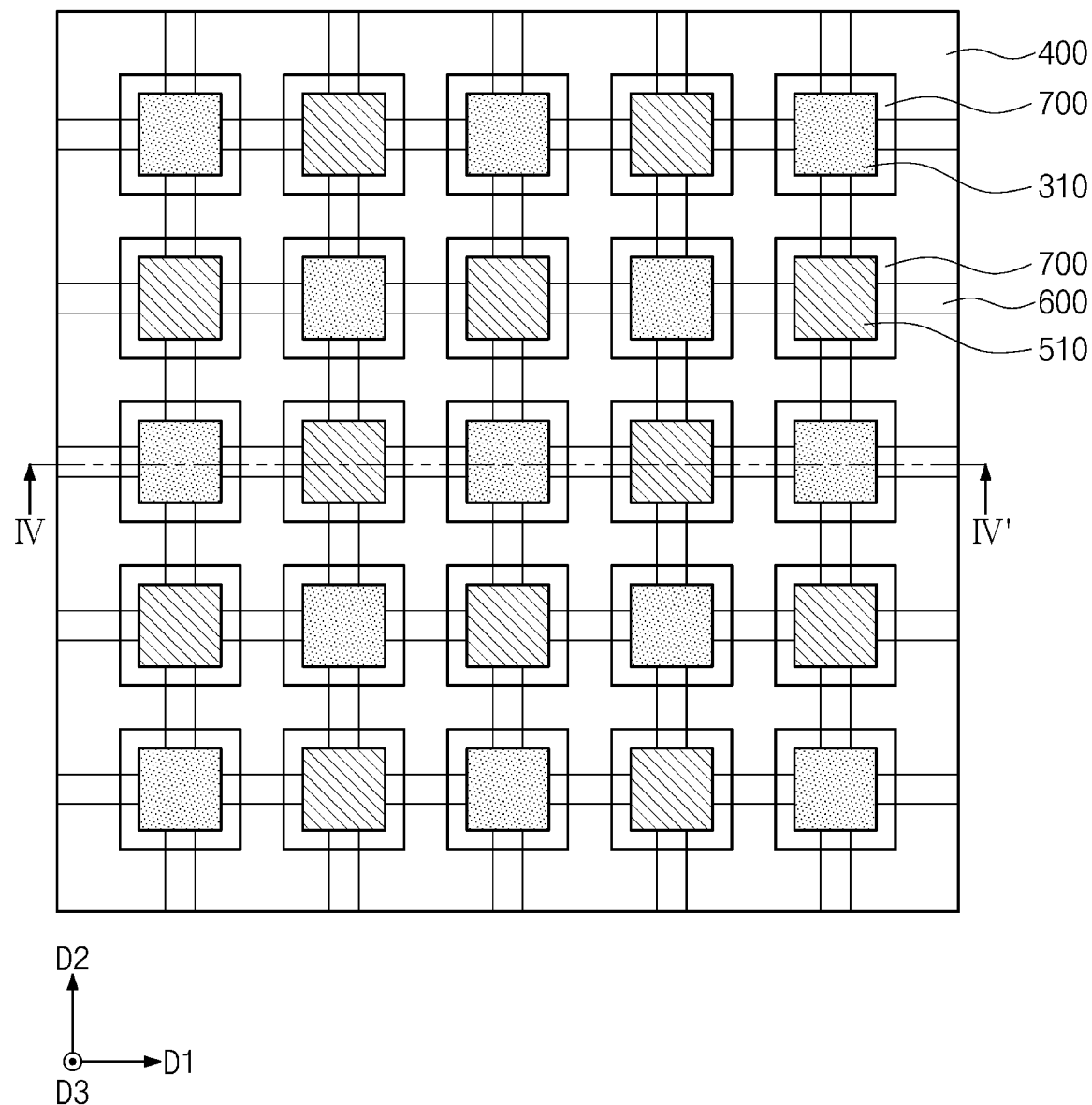
FIG. 14 is a plan view of stretchable electronics according to exemplary embodiments of the inventive concept.
Figure 15:
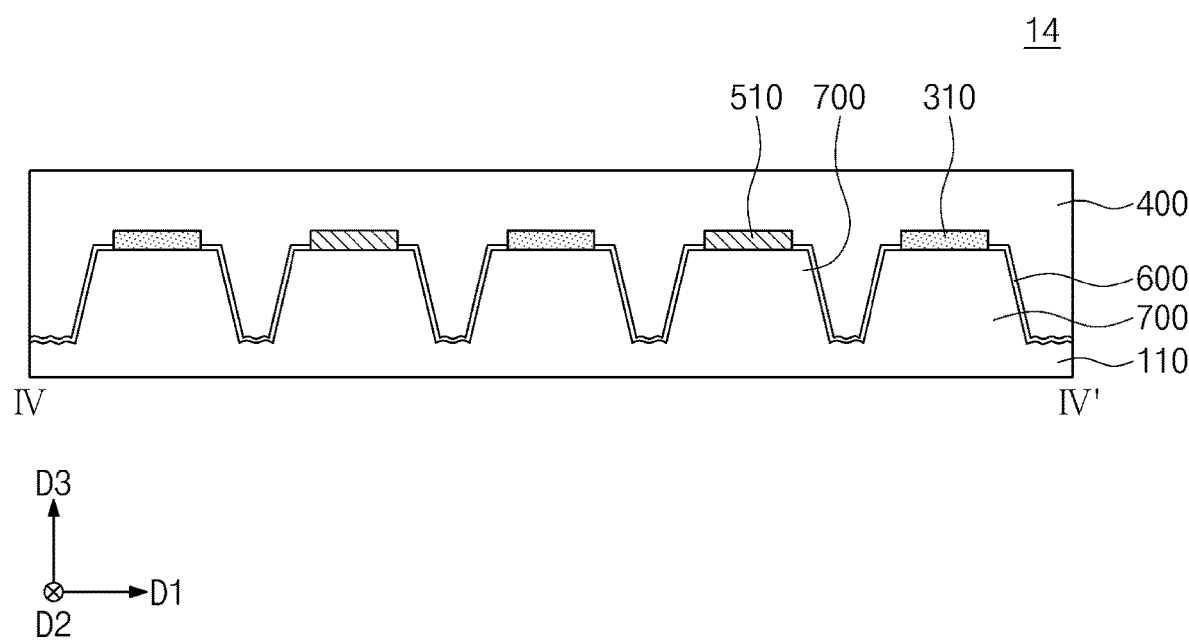
FIG. 15 is a cross-sectional view taken along line IV-IV' of FIG. 14.

FIG. 14 is a plan view of stretchable electronics according to exemplary embodiments of the inventive concept. FIG. 15 is a cross-sectional view taken along line IV-IV' of FIG. 14.

Referring to FIGS. 14 and 15, stretchable electronic 14 including a wavy substrate 110, lines 600, support patterns 700, output devices 310, input devices 510, and a protection layer 400 may be provided. The wavy substrate 110 may have stretchability. When tensile force is applied to the wavy substrate 110, the wavy substrate 110 may be expanded. For example, the wavy substrate 110 may include at least one selected from PDMS, polyimide, PMMA, silicone, and Ecoflex. The wavy substrate 110 may a wavy surface. For example, the wavy substrate 100 may have a curved top surface. When the wavy substrate 110 is expanded horizontally, wrinkles on the surface of the wavy substrate 110 may be spread.

The support patterns 700 may be disposed on the wavy substrate 110. The support patterns 700 may be arranged in a first direction D1 and a second direction D2, which are parallel to an extension direction of the wavy substrate 110. The support patterns 700 may protrude from a top surface of the wavy substrate 110 in a third direction D3 perpendicular to the extension direction of the wavy direction. The support patterns 700 may be connected to the wavy substrate 110 without a boundary therebetween. Each of the support patterns 700 may have a thickness greater than that of the wavy structure 110. That is, a distance between a top surface of the support pattern 700 and the top surface of the wavy substrate 110 may be greater than that between the top surface of the wavy substrate 110 and a bottom surface of the wavy substrate 110. Since each of the support patterns 700 has a rigid property, the support pattern 700 may have a sufficient thickness. Thus, when the wavy substrate 110 is deformed, the support pattern 700 may be maintained in, shape without being deformed. The support pattern 700 may include substantially the same material as the wavy substrate 110. For example, the wavy substrate 110 may include at least one selected from PDMS, polyimide, PMMA, silicone, and Ecoflex.

The output devices 310 and the input devices 510 may be disposed on the support patterns 700 different from each other. For example, the output devices 310 and the input device 510 may be arranged in the first direction D1 and the second direction D2.

In general, the output devices may include at least one actuator. When the actuator is directly disposed on the wavy substrate, vibration of the actuator may be absorbed to the wavy substrate. Thus, efficiency in which the vibration of the actuator is outputted to the outside of the stretchable electronics may be reduced.

The support pattern 700 according to the inventive concept may not absorb the vibration of the output device 310 including the actuator. Thus, the vibration output efficiency of the stretchable electronics 14 may be improved.

Output control devices (not shown) may be disposed between the support patterns 700 and the output devices 310. The output control devices may provide an output signal to the output devices 310. Input control devices (not shown) may be disposed between the support patterns 700 and the input devices 510. The input control devices may generate an input signal.

The lines 600 may be disposed on the wavy substrate 110 and the support pattern 700. The lines 600 may extend along a top surface of the wavy substrate 110 and side and top surfaces of the support pattern 700. The lines 600 may extend in the first direction D1 and the second direction D2 and be electrically connected to the output devices 310 and the input devices 510. The output devices 310 and the input devices 510 may be disposed on an area on which the lines 600 extending in the different directions cross each other.

Each of the lines 600 may vibrate in the third direction D3 on the top surface of the wavy substrate 110 and extend in the first direction D1 or the second direction D2. When the wavy substrate 110 is expanded horizontally to decrease in depth of the wrinkle of the wavy substrate 110, each of the lines 600 may decrease in height. Here, the lines 600 may be expanded horizontally. When the wavy substrate 110 is contracted to increase in depth of the wrinkle of the wavy substrate 110, each of the lines 600 may increase in height. Here, in view of a plane, the lines 600 may be contracted horizontally. Thus, the lines 600 may have stretchability.

When the output signal control unit (see reference numeral 6 of FIG. 1) described with reference to FIG. 1 applies an output signal to a pair of lines 600, which extend in different directions, the output device 310 crossing the pair of lines 600 may generate an output stimulation. An intensity of the output stimulation may be in proportional to an intensity of the output signal. As a result, a generated position of the output stimulation and the intensity of the output stimulation may be controlled.

When the input device 510 senses an input stimulation, the input control device may generate an input signal. The input signal may be provided to the input signal control unit 5 described with reference to FIG. 1 through the pair of lines 600 crossing the input device 510. An intensity of the input signal may be proportional to an intensity of the input stimulation received in the input device 510. As a result, a position of the input stimulation and the intensity of the input stimulation may be measured.

According to the inventive concept, the stretchable electronics 14 through which the stimulation is outputted and inputted may be provided.

Figure 16:
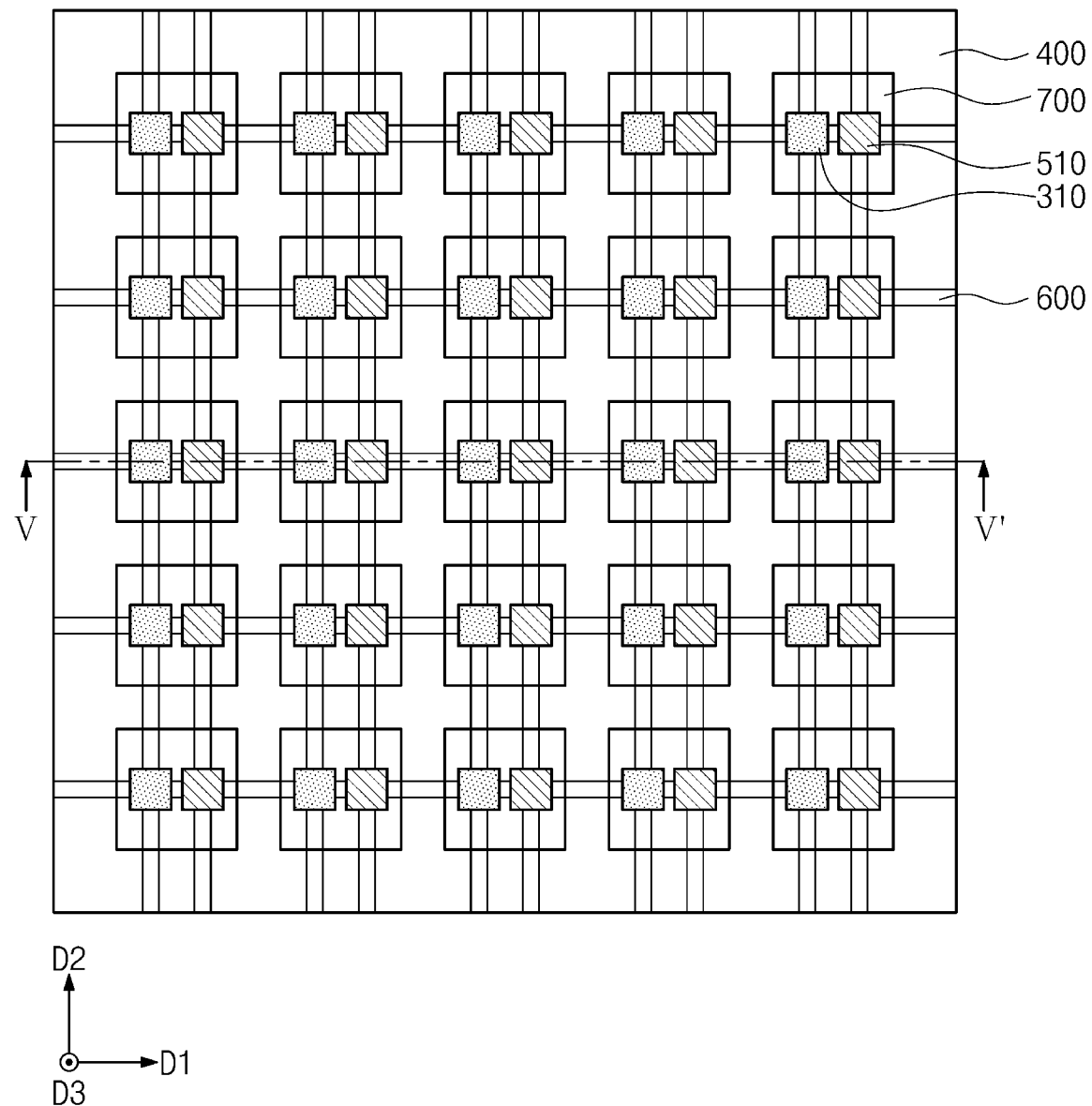
FIG. 16 is a plan view of a stretchable electronics according to exemplary embodiments of the inventive concept.
Figure 17:
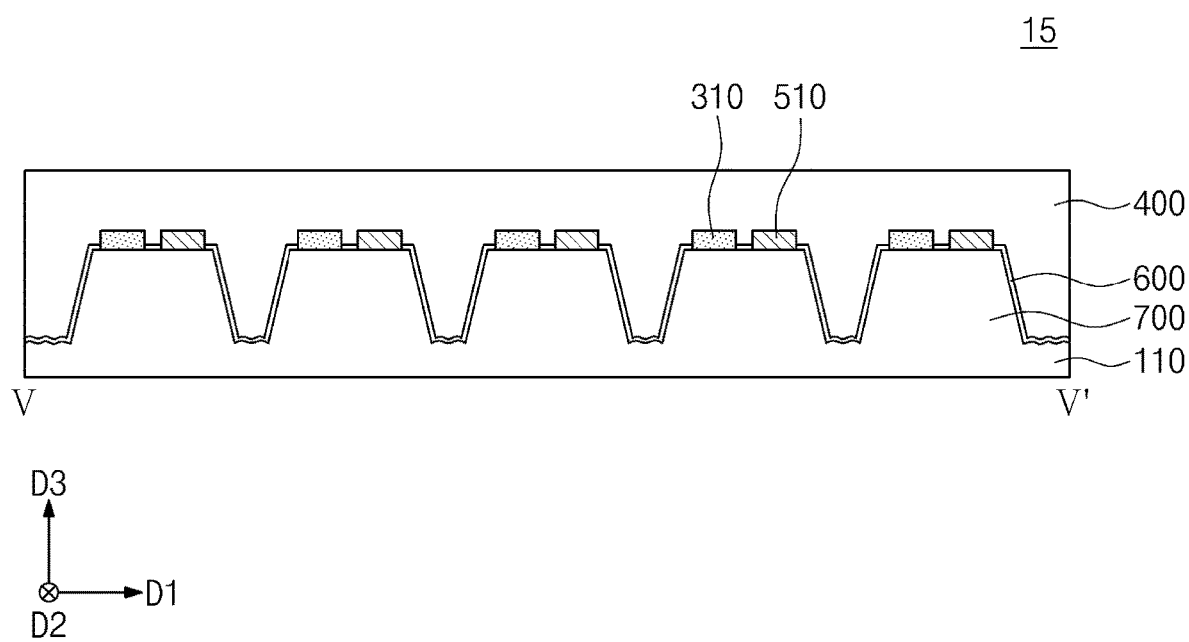
FIG. 17 is a cross-sectional view taken along line V-V' of FIG. 16.

FIG. 16 is a plan view of a stretchable electronics according to exemplary embodiments of the inventive concept. FIG. 17 is a cross-sectional view taken along line V-V' of FIG. 16. For briefness of descriptions, substantially the same description as those described with reference to FIGS. 14 and 15 will be omitted.

Referring to FIGS. 16 and 17, stretchable electronics 15 including a wavy substrate 110, lines 600, support patterns 700, output devices 310, input devices 510, and a protection layer 400 may be provided. The wavy substrate 110, the lines 600, the support patterns 700, the output devices 310, the input devices 510, and the protection layer 400 may be substantially the same as the wavy substrate 110, the lines 600, the support patterns 700, the output devices 310, the input devices 510, and the protection layer 400, which are described with reference to FIGS. 14 and 15.

Unlike FIGS. 14 and 15, a plurality of devices may be provided on one support pattern 700. For example, a structure in which the output device 310 and the input device 510 are disposed on one support pattern 700 is illustrated. For another example, two or more output devices 310 and/or two or more input devices 510 may be disposed on one support pattern 700. The output device 310 and the input device 510, which are disposed on the support pattern 700, may be spaced apart from each other in the first direction parallel to an extension direction of the wavy substrate 110. The output device 310 and the input device 510, which are disposed on the support pattern 700, may be electrically connected to each other by the lines 600.

The output devices 310 and the input devices 510 according to the inventive concept may be disposed to have high density. Thus, an output stimulation generated in the stretchable electronics 15 and an input stimulation sensed by the stretchable electronics 15 may increase in resolution.

Figure 18:
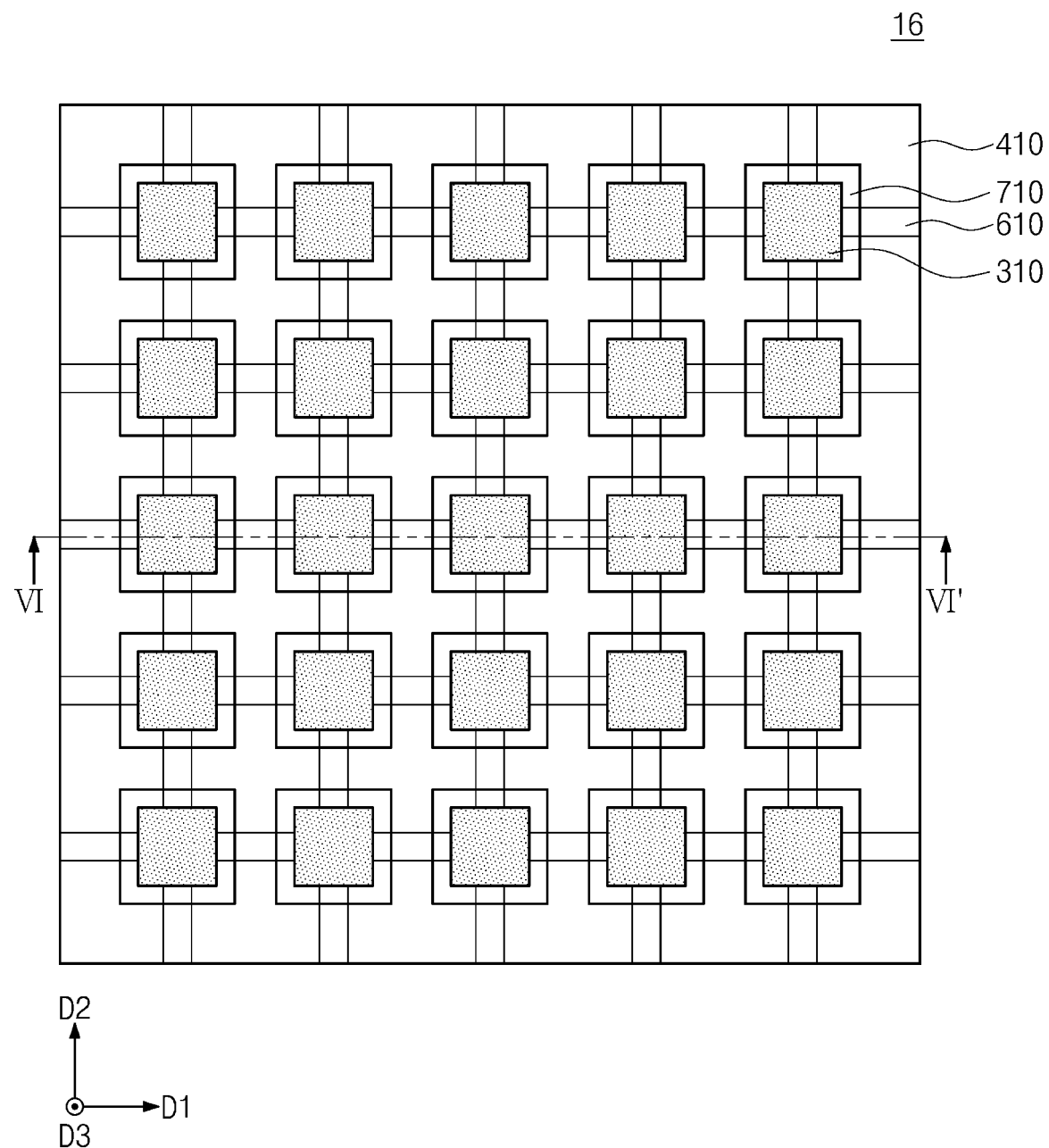
FIGS. 18 and 19 are plan and bottom views of stretchable electronics according to exemplary embodiments of the inventive concept.
Figure 19:
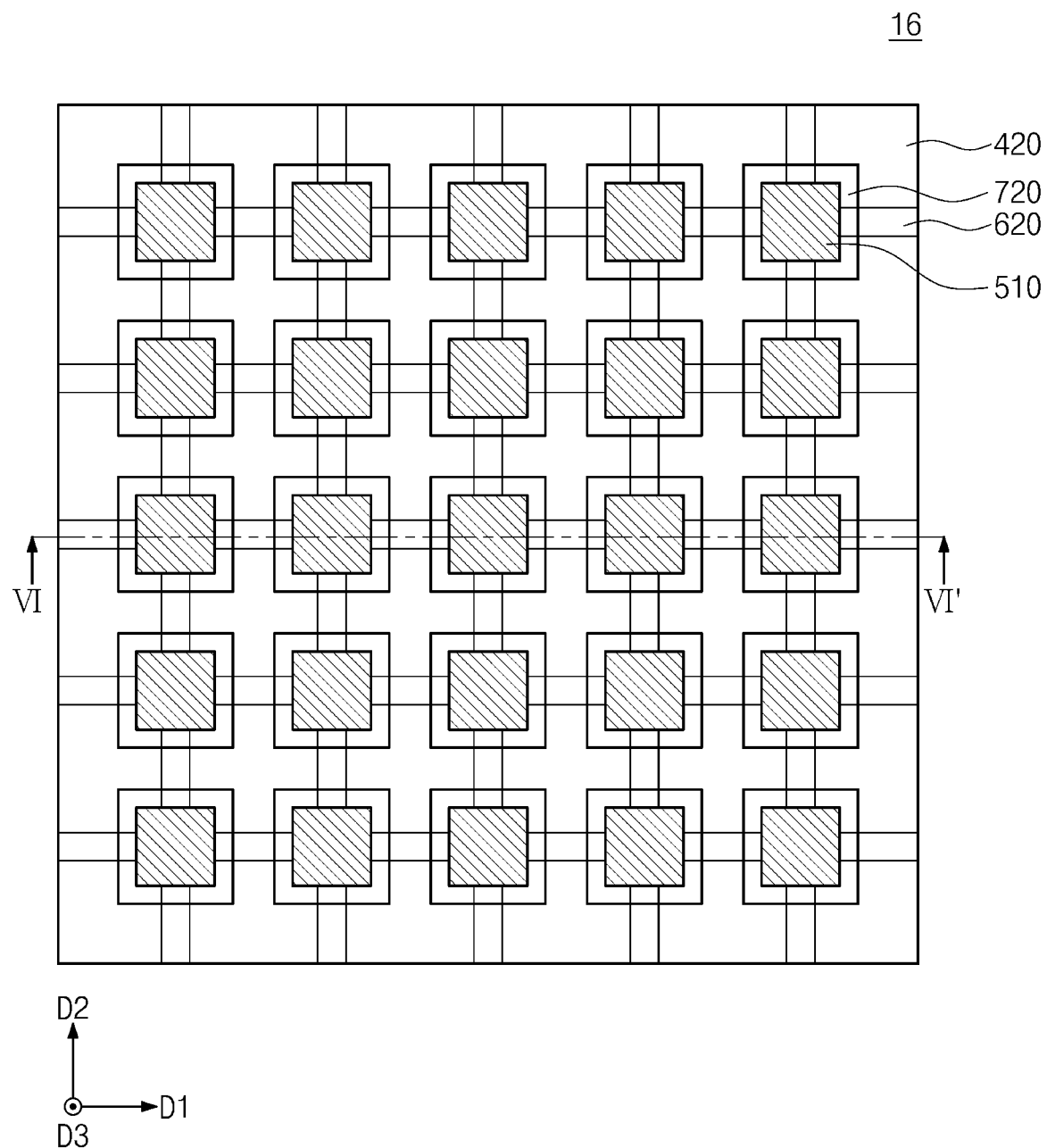
Figure 20:
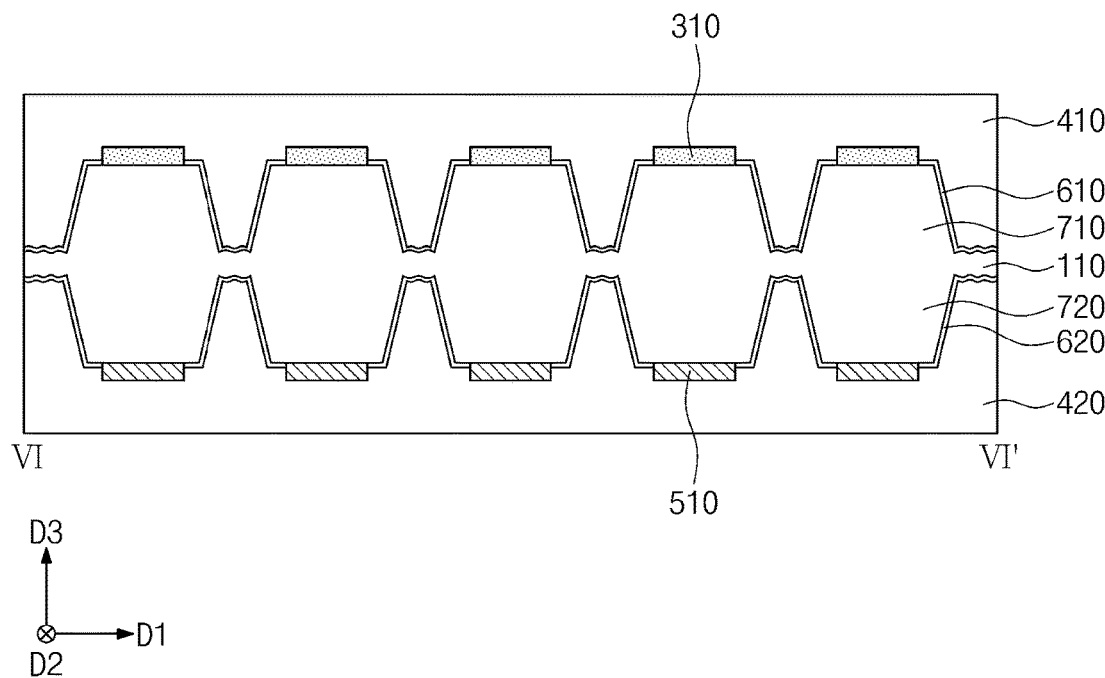
FIG. 20 is a cross-sectional view taken along line VI-VI' of FIG. 18.

FIGS. 18 and 19 are plan and bottom views of stretchable electronics according to exemplary embodiments of the inventive concept. FIG. 20 is a cross-sectional view taken along line VI-VI' of FIG. 18. For briefness of descriptions, substantially the same description as those described with reference to FIGS. 14 and 15 will be omitted.

Referring to FIGS. 18 to 20, stretchable electronics 16 including a wavy substrate 110, upper lines 610, lower lines 620, upper support patterns 710, lower support patterns 720, output devices 310, input devices 510, a first protection layer 410, and a second protection layer 420 may be provided. The wavy substrate 110 may be substantially the same as the wavy substrate 110 described with reference to FIGS. 14 to 15.

The upper support patterns 710 and the lower support patterns 720 may be substantially the same as the support patterns 700 described with reference to FIGS. 14 and 15 except for positions of the upper support patterns 710 and the lower support patterns 720. The upper support patterns 710 and the lower support patterns 720 may be disposed at sides that are opposite to each other with the wavy substrate 110 therebetween. The upper support patterns 710 may be arranged in the first direction D1 and the second direction D2, which are parallel to an extension direction of the wavy substrate 110. The upper support patterns 710 may protrude from a top surface of the wavy substrate 110 in the third direction D3 perpendicular to the extension direction of the wavy direction. The upper support patterns 710 may be disposed between the output devices 310 and the wavy substrate 110. The upper support patterns 710 may support the output devices 310, respectively.

The lower support patterns 720 may be arranged in a first direction D1 and a second direction D2, which are parallel to an extension direction of the wavy substrate 110. The lower support patterns 720 may protrude from a bottom surface of the wavy substrate 110 in the third direction D3. The lower support patterns 720 may be disposed between the input devices 510 and the wavy substrate 110. The lower support patterns 720 may support the input devices 510, respectively.

Output control devices (not shown) may be disposed between the output devices 310 and the upper support patterns 710. The output control devices may provide an output signal to the output devices 310. Input control devices (not shown) may be disposed between the input devices 510 and the lower support patterns 720. The input control devices may generate an input signal.

The upper lines 610 and the lower lines 620 may be substantially the same as the lines 600 described with reference to FIGS. 14 and 15 except for positions of the upper lines 610 and the lower lines 620. The upper lines 610 may extend along a top surface of the wavy substrate 110 and side and top surfaces of the upper support patterns 710 and be electrically connected to the output devices 310 or the output control devices. The lower lines 620 may extend along a bottom surface of the wavy substrate 110 and side and bottom surfaces of the lower support patterns 720 and be electrically connected to the output devices 310 or the output control devices.

The output devices 310 and the input device 510 may be substantially the same as the output device 310 and the input devices 510 600 described with reference to FIGS. 14 and 15 except for positions of the output devices 310 and the input device 510. The output devices 310 may be disposed on the upper support patterns 710. The input devices 510 may be disposed on the lower support patterns 720.

The first protection layer 410 and the second protection layer 420 may be substantially the same as the protection layer 400 described with reference to FIGS. 14 and 15 except for positions of the first protection layer 410 and the second protection layer 420. The first protection layer 410 may be disposed on the wavy structure 110 to cover the upper lines 610, the upper support patterns 710, and the output devices 310. The second protection layer 420 may be disposed at a side that is opposite to the first protection layer 410 with the wavy substrate 110 therebetween to cover the lower lines 620, the lower support patterns 720, and the input devices 510.

According to the inventive concept, the stretchable electronics 16 through which the stimulation is outputted and inputted may be provided.

Figure 21:
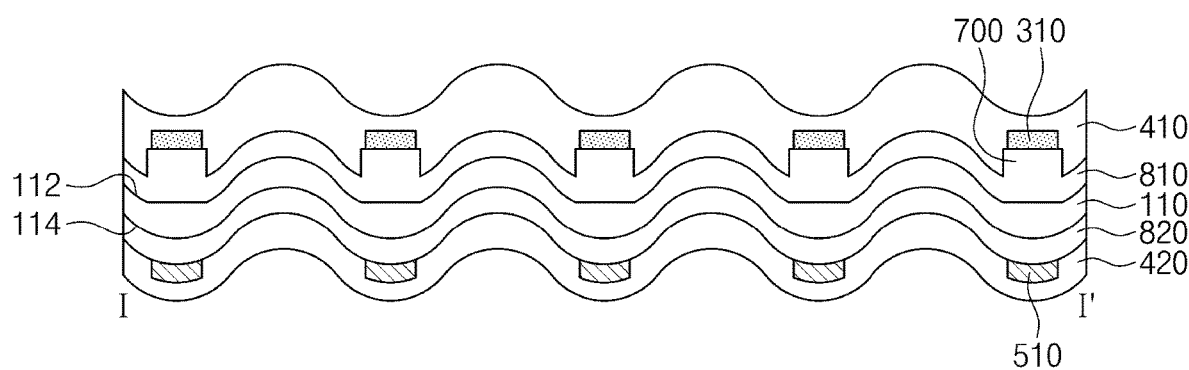
FIG. 21 is a cross-sectional view taken along line I-I' of FIG. 1 in the stretchable electronics according to exemplary embodiments of the inventive concept.

FIG. 21 is a cross-sectional view taken along line I-I' of FIG. 1 in the stretchable electronics according to exemplary embodiments of the inventive concept. For briefness of descriptions, substantially the same description as those described with reference to FIGS. 1 to 2 will be omitted.

Referring to FIG. 21, stretchable electronics 17 including a wavy substrate 110, an upper thin film 810, output devices 310, a first protection layer 410, a lower thin film 820, support patterns 700, input devices 510, and a second protection layer 420 may be provided. The wavy substrate 110 may have a first surface 112 and a second surface 114, which face each other. Each of the first surface 112 and the second surface 114 may have a wavy shape. The wavy substrate 110 may have stretchability. For example, the wavy substrate 110 may include an elastomer.

The upper thin film 810 and the lower thin film 820 may be disposed on the first surface 112 and the second surface 114 of the wavy substrate 110, respectively. The upper thin film 810 and the lower thin film 820 may extend along the first surface 112 and the second surface 114, respectively. Thus, each of the upper thin film 810 and the lower thin film 820 has a wavy shape. Each of the upper thin film 810 and the lower thin film 820 may have stretchability. For example, each of the upper thin film 810 and the lower thin film 820 may include at least one selected from PDMS, polyimide, PMMA, silicone, and Ecoflex.

The support patterns 700 may be disposed on the upper thin film 810. The support patterns 700 may be arranged along a top surface of the upper thin film 810. Although the support patterns 700 are provided for peaks of the upper thin film 810, but this is merely an example. That is, the position of the support patterns 700 may not be limited to the peaks of the upper thin film 810.

The support patterns 700 may protrude from the top surface of the upper thin film 810 in a direction perpendicular to the extension direction of the wavy substrate 110. The support patterns 700 may be connected to the upper thin film 810 without a boundary therebetween. Each of the support patterns 700 may have a thickness greater than that of the upper thin film 810. That is, a distance between a top surface of the support pattern 700 and the top surface of the upper thin film 810 may be greater than that between the top surface of the upper thin film 810 and a bottom surface of the upper thin film 810. Since each of the support patterns 700 has a rigid property, the support pattern 700 may have a sufficient thickness. Thus, when the upper thin film 810 is deformed, the support pattern 700 may be maintained in shape without being deformed. Each of the support patterns 700 may include substantially the same material as the upper thin film 810. For example, the wavy substrate 110 may include at least one selected from PDMS, polyimide, PMMA, silicone, and Ecoflex.

The output devices 310 may be disposed on the support patterns 700. Output control devices (not shown) may be disposed between the output devices 310 and the support patterns 700. The output control devices may control output devices 310, respectively. Upper lines (not shown) may be disposed on the upper thin film 810. The upper lines may extend along the top surface of the upper thin film 810 and be electrically connected to the output devices 310 or the output control devices.

Input devices 510 may be disposed on the lower thin film 820. The input devices 510 may be arranged along a bottom surface of the lower thin film 820. Although the input devices 510 are provided for valleys of the lower thin film 820, but this is merely an example. The position of the input devices 510 may not be limited to the valleys of the lower thin film 820. Input control devices (not shown) may be disposed between the input devices 510 and the lower thin film 820. The input control devices may control the input devices 510, respectively. Lower lines (not shown) may be disposed on the lower thin film 820. The lower lines may extend along the bottom surface of the lower thin film 820 and be electrically connected to the input control devices.

The first protection layer 410 and the second protection layer 420 may be disposed at sides that are opposite to each other with the wavy substrate 110 therebetween. The first protection layer 410 may be disposed on the output devices 310, the support patterns 700, and the upper thin film 810. The first protection layer 410 may extend along the top surface of the upper thin film 810 to cover the support patterns 700 and the output devices 310. The second protection layer 420 may be disposed on the input devices 510 and the lower thin film 820. The second protection layer 420 may extend along the bottom surface of the lower thin film 820 to cover the input devices 510.

According to the inventive concept, the stretchable electronics 17 through which the stimulation is outputted and inputted may be provided.

FIG. 21 is a cross-sectional view taken along line I-I' of FIG. 1 so as to explain the method for fabricating the stretchable electronics according to exemplary embodiments of the inventive concept. For briefness of descriptions, substantially the same description as those described with reference to FIGS. 4 to 7 will be omitted.

Figure 22:
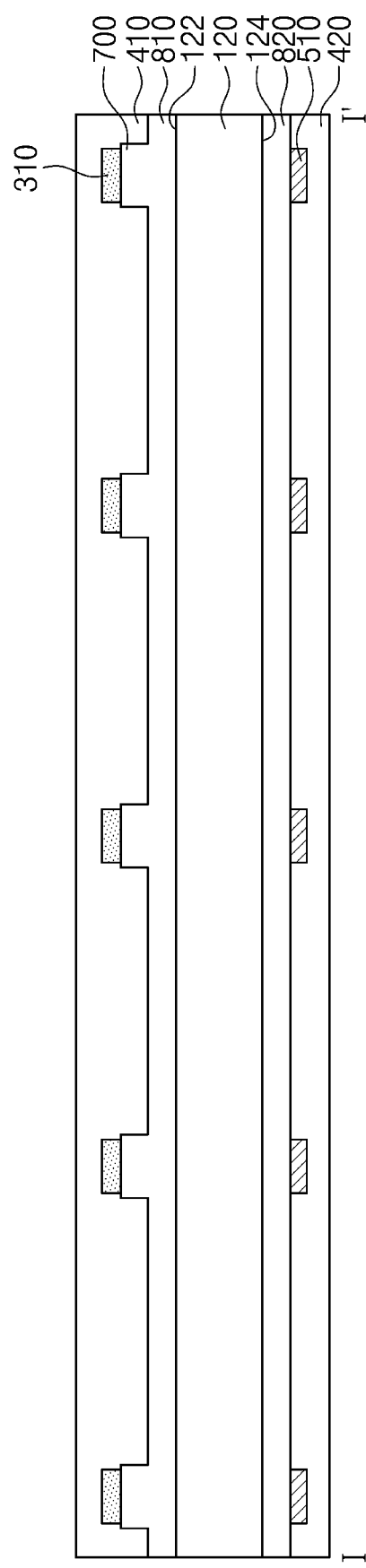
FIG. 22 is a cross-sectional view taken along line I-I' of FIG. 1 so as to explain the method for fabricating the stretchable electronics according to exemplary embodiments of the inventive concept.

Referring to FIG. 22, an upper thin film 810, support patterns 700, output devices 310, and a first protection layer 410 may be formed on a first surface 122 of a preliminary wavy substrate 120. The preliminary wavy substrate 120 may have stretchability. For example, the preliminary wavy substrate 120 may include an elastomer. The preliminary wavy substrate 120 may be a pre-stretched film. The preliminary wavy substrate 120 may have a first surface 122 and a second surface 124, which face each other. The first surface 122 and the second surface 124 may be flat surfaces.

A process of forming the upper thin film 810, the support patterns 700, the output devices 310, and the first protection layer 410 may include a process of separating the upper thin film 810 to the first protection layer 410 from a carrier substrate (not shown) so as to be transferred to the first surface 122 of the preliminary wavy substrate 120 after the upper thin film 810, the support patterns 700, the output devices 310, and the first protection layer 410 are formed on the carrier substrate. While the upper thin film 810, the support patterns 700, the output devices 310, the first protection layer 410 are transferred, the preliminary wavy substrate 120 may be subjected to tensile force in the extension direction of the preliminary wavy substrate 120. Thus, the first surface 122 may be maintained in a flat shape. That is, the preliminary wavy substrate 120 may not have wrinkles.

A lower thin film 820, input devices 510, and a second protection layer 420 may be formed on a second surface 124 of the preliminary wavy substrate 120. A process of forming the lower thin film 820, the input devices 510, and the second protection layer 420 may include a process of separating the lower thin film 820 to the second protection layer 420 from a carrier substrate (not shown) so as to be transferred to the second surface 124 of the preliminary wavy substrate 120 after the lower thin film 820, the input devices 510, and the second protection layer 420 are formed on the carrier substrate. While the lower thin film 820, the input devices 510, the second protection layer 420 are transferred, the preliminary wavy substrate 120 may be subjected to tensile force in the extension direction of the preliminary wavy substrate 120. Thus, the second surface 124 may be maintained in a flat shape. That is, the preliminary wavy substrate 120 may not have wrinkles.

Referring to FIG. 21, the tensile force may be removed from the preliminary wavy substrate (see reference numeral 120 of FIG. 22) so that the preliminary wavy substrate (see reference numeral 120 of FIG. 22) is contracted. Thus, wrinkles may be formed on the preliminary wavy substrate (see reference numeral 120 of FIG. 22). That is, the wavy substrate 110 may be provided. As a result, each of the upper thin film 810, the lower thin film 820, the first protection layer 410, and the second protection layer 420 may have a wavy structure.

According to the inventive concept, each of the wavy substrate 110, the upper thin film 810, the lower thin film 820, the first protection layer 410, and the second protection layer 420 may have stretchability due to the wavy structure thereof. Thus, the stretchable electronics 17 may be provided.

Figure 23:
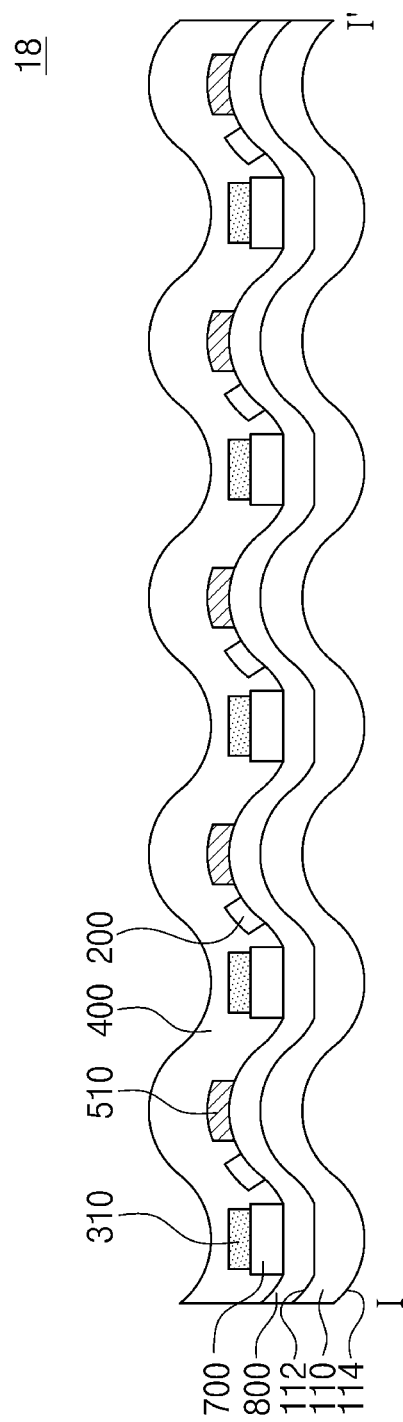
FIG. 23 is a cross-sectional view taken along line I-I' of FIG. 1 in the stretchable electronics according to exemplary embodiments of the inventive concept.

FIG. 23 is a cross-sectional view taken along line I-I' of FIG. 1 in the stretchable electronics according to exemplary embodiments of the inventive concept. For briefness of descriptions, substantially the same description as those described with reference to FIG. 21 will be omitted.

Referring to FIG. 23, stretchable electronics 18 including a wavy substrate 110, a thin film 800, output devices 310, control devices 200, support patterns 700, input devices 510, and protection layer 400 may be provided. The wavy substrate 110, the thin film 800, the output devices 310, the support patterns 700, and the protection layer 400 may be substantially the same as the wavy substrate 110, the thin film 800, the output devices 310, the support patterns 700, and the protection layer 400, which are described with reference to FIG. 21.

The input devices 510 may be substantially the same as the input devices 510 described with reference to FIGS. 2 to 4 except for a position of each of the input devices 510. The input devices 510 may be disposed on the thin film 800. For example, each of the input devices 510 may be disposed between the output devices 310 that are adjacent to each other.

Control devices 200 may be disposed on the thin film 800. In the exemplary embodiments, each of the control devices 200 may control the output device 310 and the input device 510.

According to the inventive concept, the stretchable electronics 18 through which the stimulation is outputted and inputted may be provided.

Figure 24:
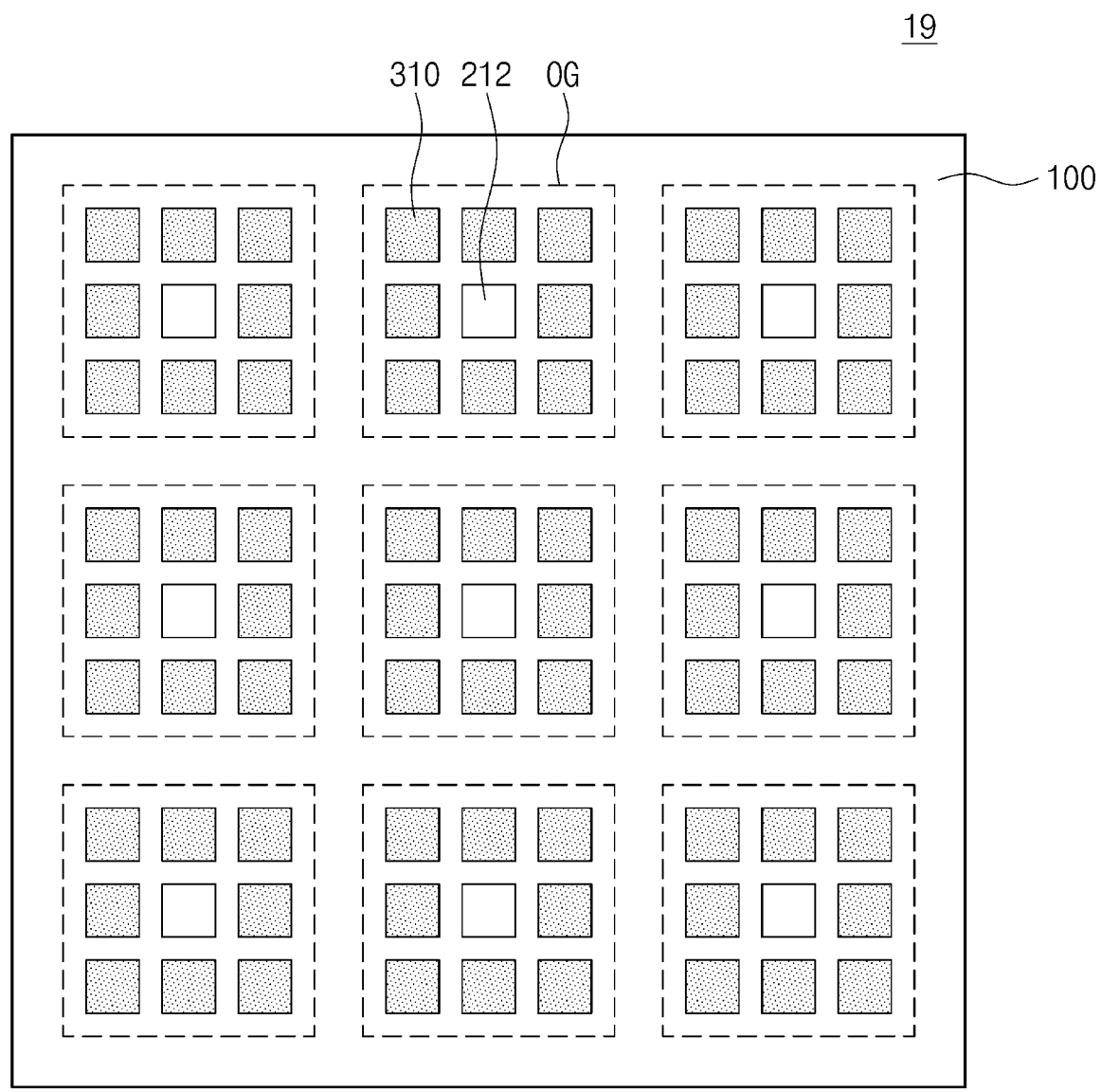
FIGS. 24 and 25 are plan and bottom views of stretchable electronics according to exemplary embodiments of the inventive concept.
Figure 25:
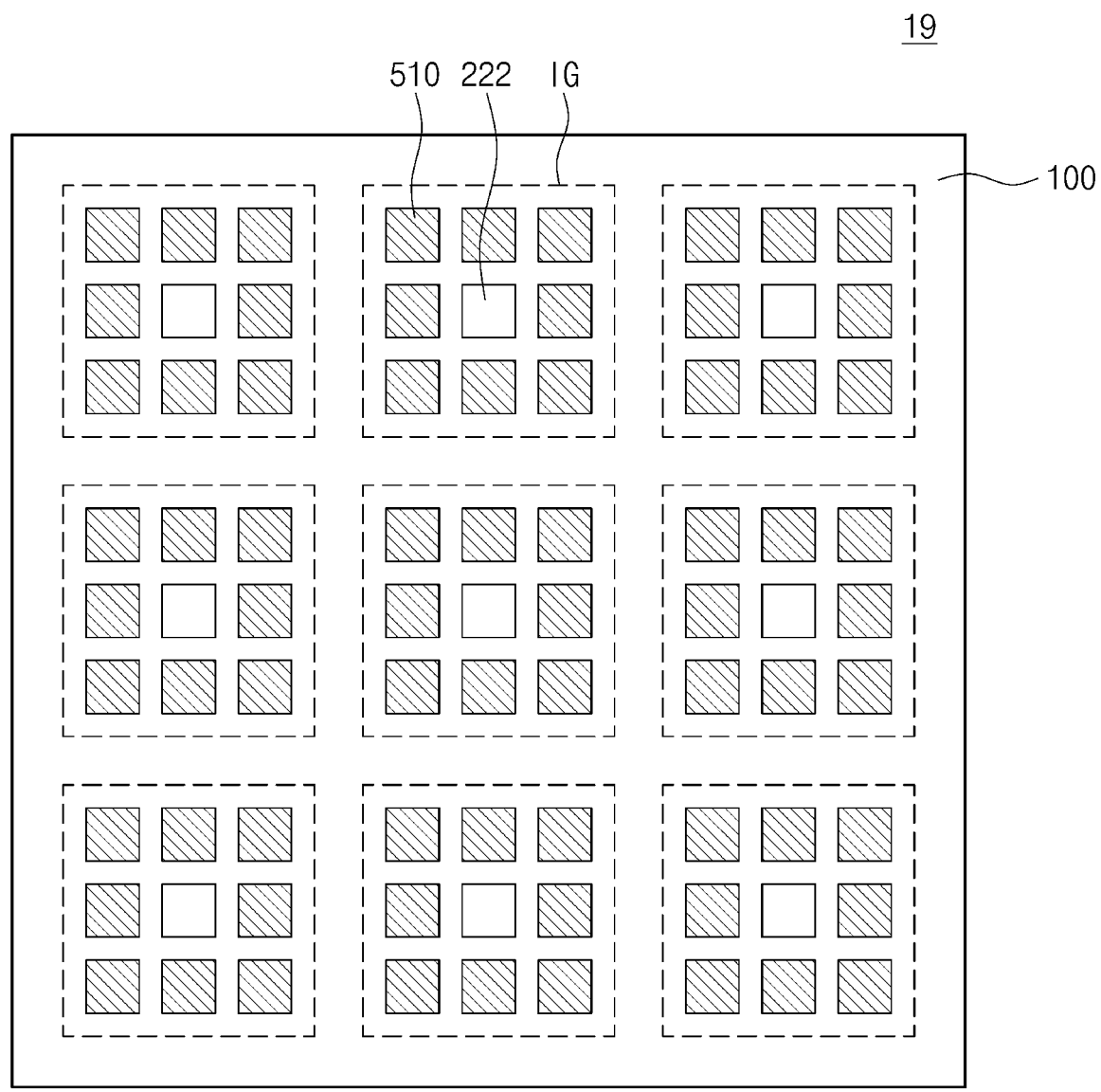

FIGS. 24 and 25 are plan and bottom views of stretchable electronics according to exemplary embodiments of the inventive concept. For briefness of descriptions, substantially the same description as those described with reference to FIGS. 2 to 4 will be omitted.

Referring to FIGS. 24 and 25, stretchable electronics 19 including a substrate 100, output groups OG, and input group IG may be provided. The substrate 100 may be substantially the same as the substrate 100 described with reference to FIGS. 2 to 4. Each of the output groups OG may include output devices 310 and an output control device 212. The output devices 310 may be controlled to output the same stimulation at the same time by the output control device 212. Thus, the stretchable electronics 19 may increase in sensory output intensity.

Each of the input groups IG may include input devices 510 and an input control device 222. The input devices 510 may sense the same stimulation at the same time to provide the sensed stimulation to the input control device 222. Thus, the stretchable electronics 19 may increase in stimulation sensing sensitivity.

According to the inventive concept, the stretchable electronics 19 through which the stimulation is outputted and inputted may be provided.

According to the inventive concept, the stretchable electronics through which the stimulation is outputted and inputted may be provided.

According to the inventive concept, the stretchable electronics may be improved in sensory transmission efficiency.

According to the inventive concept, the stretchable electronics may be easily fabricated.

However, the effects of the inventive concept are not limited to the above-described descriptions.

The above-described descriptions according to the embodiments of the inventive concept are exemplarily provided for explaining the inventive concept. Thus, it is understood that the present invention should not be limited to these exemplary embodiments but various changes and modifications can be made by one ordinary skilled in the art within the spirit and scope of the present invention as hereinafter claimed.

What is claimed is:

1. Stretchable electronics comprising:
 a stretchable substrate;
 first support patterns disposed on a first surface of the stretchable substrate; and
 output devices disposed on the first support patterns, respectively,
 wherein
 the first support patterns are arranged in a first direction and a second direction, which are parallel to an extension direction of the substrate,
 each of the output devices generates an output stimulation,
 at least one of the output devices comprises
  actuators disposed on the first support patterns, and
  a diaphragm disposed on the actuators,
 the diaphragm is spaced apart from the first support patterns by the actuators, and
 the diaphragm vibrates by movement of the actuators.

2. The stretchable electronics of claim 1, wherein the first support patterns protrude from the first surface of the stretchable substrate.

3. The stretchable electronics of claim 1, wherein each of the first support patterns has a thickness greater than a thickness of the stretchable substrate.

4. The stretchable electronics of claim 1, wherein each of the first support patterns comprises a same material as a material within the stretchable substrate and has a rigid property.

5. The stretchable electronics of claim 1, wherein the first surface comprises a wavy surface.

6. The stretchable electronics of claim 5, further comprising lines disposed on the stretchable substrate and the first support patterns,
wherein the lines extend along the wavy surface of the first surface.

7. The stretchable electronics of claim 6, wherein each of the lines has a straight line shape on a side surface of the first support patterns and has a winding shape on the first surface.

8. The stretchable electronics of claim 6, wherein the lines comprise:
first lines extending in the first direction; and
second lines extending in the second direction,
wherein the output devices are disposed on areas on which the first lines and the second lines cross each other, respectively.

9. The stretchable electronics of claim 1, further comprising input devices disposed on the first surface,
wherein the input devices and the output devices are alternately arranged in the first direction and the second direction, and
the input devices sense an input stimulation.

10. The stretchable electronics of claim 9, further comprising second support patterns disposed between the input devices and the first surface,
wherein the second support patterns protrude from the first surface.

11. The stretchable electronics of claim 9, further comprising:
an output signal control unit; and
an input signal control unit,
wherein the output devices generate the output stimulation on the basis of an output signal provided from the output signal control unit, and
the input devices generate input signals corresponding to the input stimulation to provide the input signals to the input signal control unit,
wherein the output signal comprises position information and intensity information of the output stimulation, and
the input signal comprises position information and intensity information of the input stimulation.

12. The stretchable electronics of claim 1, further comprising input devices disposed on a second surface of the stretchable substrate, which faces the first surface,
wherein the input devices are alternately arranged in the first direction and the second direction, and
the input devices sense an input stimulation.

13. The stretchable electronics of claim 12, further comprising second support patterns disposed between the input devices and the second surface,
wherein the second support patterns protrude from the second surface.

14. The stretchable electronics of claim 13, wherein each of the second support patterns comprises a same material as a material within the stretchable substrate and has a rigid property.

15. The stretchable electronics of claim 13, wherein the second surface comprises a wavy surface.

16. A method for fabricating stretchable electronics, the method comprising:
forming an output device structure having support patterns on a first carrier substrate, the support patterns being arranged in a first direction and a second direction parallel to an extension direction of the first carrier substrate;
separating the output device structure from the first carrier substrate so as to be transferred to a first surface of a stretchable substrate;
forming an input device structure on a second carrier substrate; and
separating the input device structure from the second carrier substrate so as be transferred to a second surface of the stretchable substrate, which is opposite the first surface,
wherein
the output device structure comprises output devices generating an output stimulation,
the input device structure comprises input devices receiving an input stimulation,
at least one of the output devices comprises
actuators disposed on the support patterns, and
a diaphragm disposed on the actuators,
the diaphragm is spaced apart from the support patterns by the actuators, and
the diaphragm vibrates by movement of the actuators.

17. The method of claim 16, further comprising providing tensile force to the stretchable substrate while the output device structure and the input device structure are transferred to the stretchable substrate.

18. The method of claim 17, further comprising removing the tensile force from the stretchable substrate to form a wavy structure on the stretchable substrate after the transferring of the output device structure and the input device structure on the stretchable substrate.

19. The method of claim 18, wherein the stretchable substrate comprises an elastomer.

* * * * *